(12) United States Patent
Croce

(10) Patent No.: US 9,212,396 B2
(45) Date of Patent: *Dec. 15, 2015

(54) MATERIALS AND METHODS USEFUL FOR AFFECTING TUMOR CELL GROWTH, MIGRATION AND INVASION

(71) Applicant: The Ohio State University, Columbus, OH (US)

(72) Inventor: Carlo M. Croce, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,118

(22) Filed: Dec. 19, 2014

(65) Prior Publication Data

US 2015/0104412 A1    Apr. 16, 2015

Related U.S. Application Data

(63) Continuation of application No. 13/511,474, filed as application No. PCT/US2010/057758 on Nov. 23, 2010, now Pat. No. 8,916,533.

(60) Provisional application No. 61/263,655, filed on Nov. 23, 2009.

(51) Int. Cl.
*A61K 48/00* (2006.01)
*C12Q 1/68* (2006.01)
*A61K 38/19* (2006.01)

(52) U.S. Cl.
CPC ............ *C12Q 1/6886* (2013.01); *A61K 38/191* (2013.01); *C12Q 1/6876* (2013.01); *C12Q 2600/106* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

PUBLICATIONS

Mercatelli et al. (PLoS One, Dec. 2008, vol. 3: e4029 1-10 of record).*
Munshi et al. (Cancer Chemother Pharmacol (2002) 50: 46-52).*
Yang et al. (of record).*
Rhodes et al. (Cancer Research 62, 2002: 4427-4433).*
Galardi et al. (JBC 2007, Col. 282:23716-23724).*

* cited by examiner

*Primary Examiner* — Kimberly Chong
(74) *Attorney, Agent, or Firm* — MacMillan, Sobanski & Todd, LLC

(57) ABSTRACT

It is disclosed herein that miR-221 and miR-222 down-regulate PTEN and TIMP3 tumor suppressors, resulting in TRAIL resistance. The present invention provides research, diagnostic, and therapeutic tools and methods related to this discovery. Diagnostics, prognostics and treatments for human hepatocellular cancer and non-small cell lung carcinoma having a TRAIL resistance are particularly described herein.

24 Claims, 24 Drawing Sheets
(22 of 24 Drawing Sheet(s) Filed in Color)

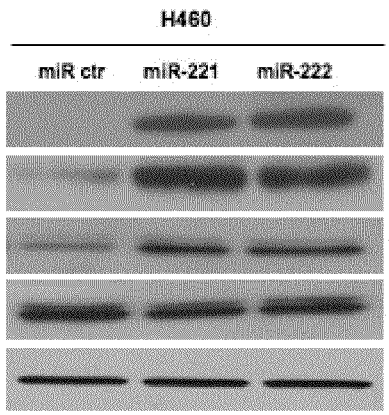
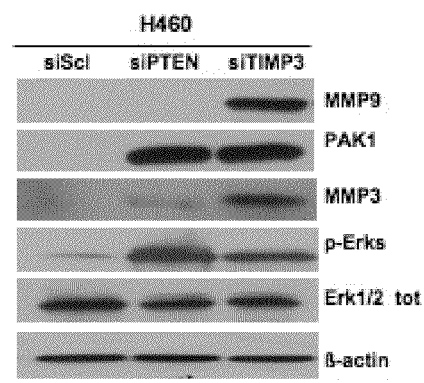
Figure 5C    Figure 5D
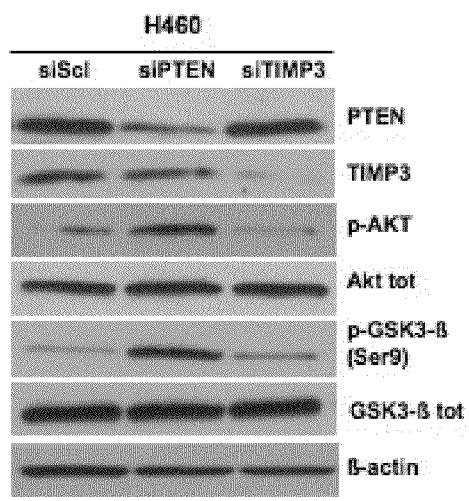
Figure 5E
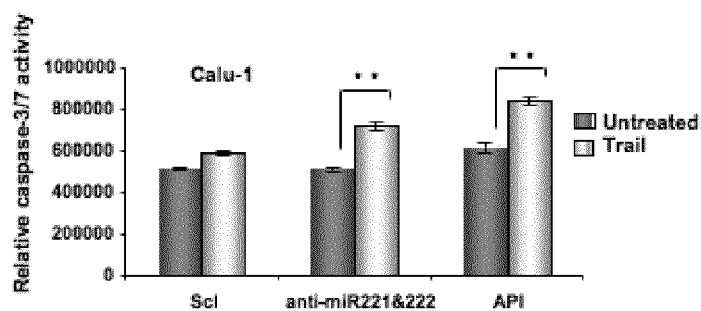
Figure 5F

MIGRATION

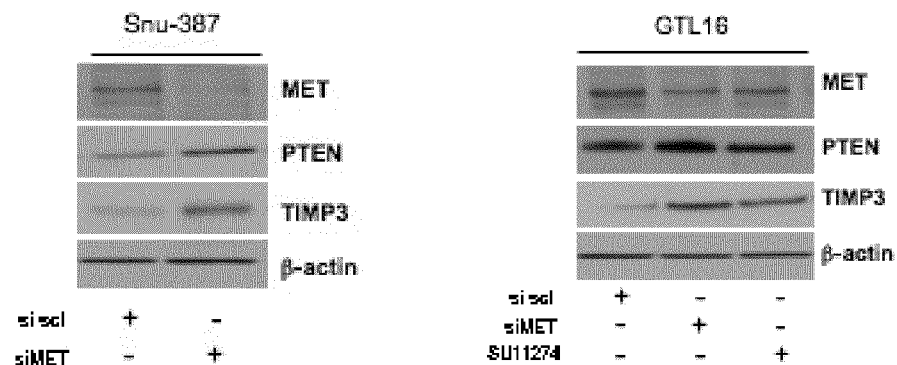
Figure 7E          Figure 7F
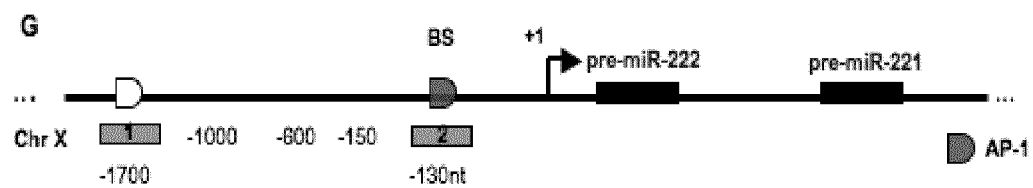
Figure 7G
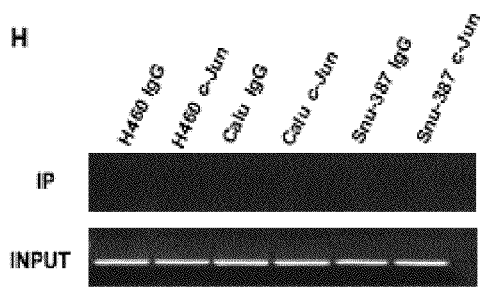          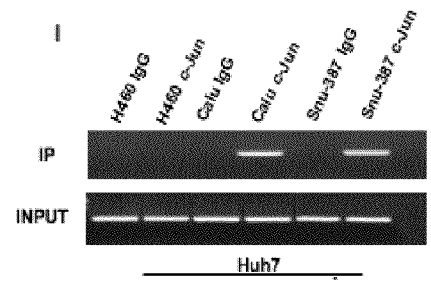
Figure 7H          Figure 7I

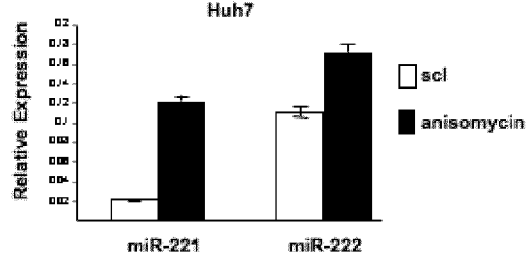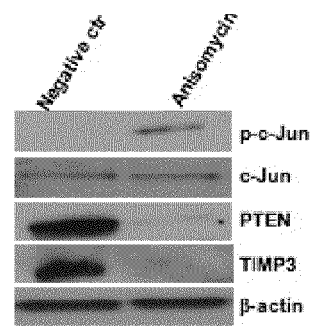
Figure 7J        Figure 7K
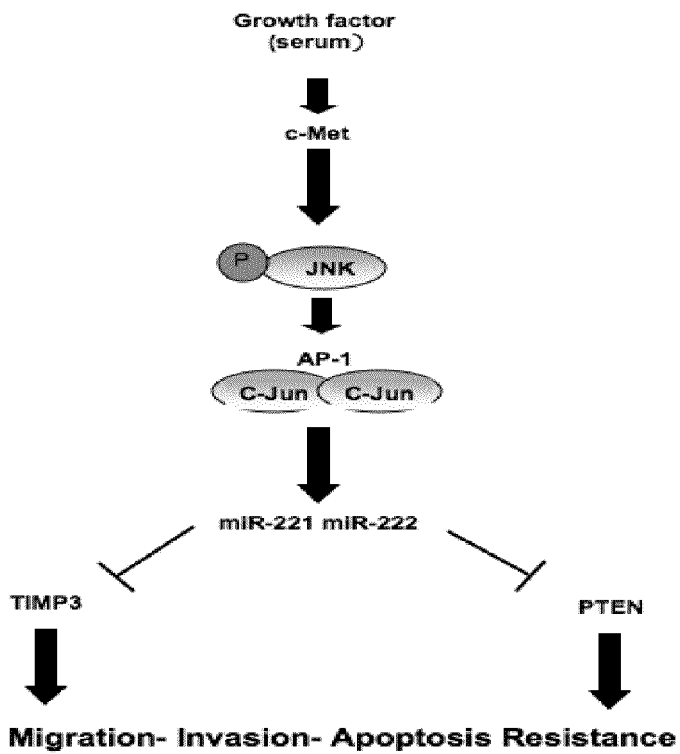
Figure 8 ial Application No. 61/263,655, filed Nov. 23, 2009,

SEQUENCE LISTING

```
<160> NUMBER OF SEQ ID NOS: 31

<210> SEQ ID NO 1
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
tctagagact ctgatccaga gaatgaacc                                       29

<210> SEQ ID NO 2
<211> LENGTH: 36
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 2
tctagagttg ccacaagtgc aaagggggtag gatgtg                              36

<210> SEQ ID NO 3
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
tctagactgg gcaaagaagg gtctttcgca aagc                                34

<210> SEQ ID NO 4
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
tctagattcc aatagggagg aggctggagg agtctc                              36

<210> SEQ ID NO 5
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gttgaaaaaa ggttgggggc gggtgtcatg tatatac                             37

<210> SEQ ID NO 6
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
gtatatacat gacacccgcc cccaaccttt tttcaac                             37

<210> SEQ ID NO 7
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gtataattta aaatcattgg gcggcgggag acacttctgt atttc                    45
```

```
<210> SEQ ID NO 8
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
gaaatacaga agtgtctccc gccgcccaat gattttaaat tatac           45

<210> SEQ ID NO 9
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gctagcccta gccaccttat cgaaaatagc attcc                      35

<210> SEQ ID NO 10
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gctagcctga catgctagtg agcacctgc                             29

<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
gctagcccag aggttgttta aaattacgta                            30

<210> SEQ ID NO 12
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ctcgagagct gggtgatcct ttgccttctg                            30

<210> SEQ ID NO 13
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

<400> SEQUENCE: 13
gaaacccagc agacaatgta gct                                            23

<210> SEQ ID NO 14
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 14
gagacccagt agccagatgt agct                                           24

<210> SEQ ID NO 15
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gaaacccagc agacaaugua gcu                                            23

<210> SEQ ID NO 16
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gagacccagt agccagatgt agct                                           24

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
aaggcaagcu gacccugaag u                                              21

<210> SEQ ID NO 18
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gatgtggaga atagatacct ttgag                                          25

<210> SEQ ID NO 19
<211> LENGTH: 25
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 19
ggcactgcct acaaaccaga gcata                                           25

<210> SEQ ID NO 20
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gtcactcagt cagtatctgt tgga                                            24

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
gtgtgtaatt caaggtaaag ttttc                                           25

<210> SEQ ID NO 22
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
gcggccgcat gaccccttgg ctcgggctca tcgtgct                              37

<210> SEQ ID NO 23
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
agatctcagg gtctggcgct cagggtctg t                                     31

<210> SEQ ID NO 24
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gcggccgcat gacagccatc atcaaagaga tcgttag                              37
```

```
<210> SEQ ID NO 25
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
tctagaggtg ttttatccct cttgataaaa aaaaattca                              39

<210> SEQ ID NO 26
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
agcuacaucu ggcuacuggg uc                                                22

<210> SEQ ID NO 27
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
cagttgaaaa aaggttgtgt agctgtg                                           27

<210> SEQ ID NO 28
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
agcuacauug ucucgcuggg guuuc                                             25

<210> SEQ ID NO 29
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cagttgaaaa aaggttggcg gcgggtg                                           27

<210> SEQ ID NO 30
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 30
auuuaaaauc auuuauguag cugag                                    25

<210> SEQ ID NO 31
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
auuuaaaauc auuuggcggc gggag                                    25
```

MATERIALS AND METHODS USEFUL FOR AFFECTING TUMOR CELL GROWTH, MIGRATION AND INVASION

CROSS-REFERENCE TO RELATED APPLICATIONS

This application is a divisional application of U.S. Ser. No. 13/511,474 filed Jun. 8, 2012, now U.S. Pat. No. 8,916,533 issued Dec. 23, 2014, which claims priority to PCT/US2010/057758 filed Nov. 23, 2010, which claims the benefit of U.S. Provisthe disclosure of which is incorporated herein by reference.

STATEMENT REGARDING FEDERALLY SPONSORED RESEARCH

This invention was not made with any government support and the government has no rights in this invention.

FIELD OF THE INVENTION

This invention relates generally to the field of molecular biology. More particularly, it concerns cancer-related technology. Certain aspects of the invention include application in diagnostics, therapeutics, and prognostics related to miR-221 and miR-222. In particular liver cancer and lung cancer diagnostics, therapeutics and prognostics are discussed herein.

The present invention is partially based on the discovery that:

binding of hepatocyte growth factor to the hepatocyte growth factor receptor (MET) upregulates phosphorylation of an extracellular signal-regulated kinase (ERK1/2) and Jun N-termal kinase (JNK), which, in turn, upregulates Jun transcriptional activation, which, in turn, upregulates expression of non-coding microRNAs (miR-221 and miR-222), which, in turn, down regulates expression of phosphatase and tensin homolog (PTEN) and tissue inhibitor of metalloproteinase 3 (TIMP3), which, in turn, confers resistance to tumor necrosis factor-related apoptosis-inducing ligand (TRAIL)-induced cell death and enhances tumorigenicity of lung and liver cancer cells.

The present invention provides research tools, diagnostic methods, and therapeutical methods and compositions using the knowledge derived from this discovery. The invention is industrially applicable for the purpose of sensitizing tumor cells to drug-inducing apoptosis and also to inhibit tumor cell survival, proliferation and invasive capabilities.

BACKGROUND OF THE INVENTION

Despite advances in early detection and standard treatment, non small cell lung cancer (NSCLC) and hepatocellular carcinoma (HCC), are often diagnosed at an advanced stage and have poor prognoses. Promoting apoptosis is a possible goal for drug development. TNF-related apoptosis-inducing ligand (TRAIL) is currently being tested in clinical trials; however the resistance of many tumors, including NSCLC and HCC, to TRAIL represent obstacles to its clinical application.

miRNAs are small non-coding RNAs of 19-25 nt that can block mRNA translation and/or negatively regulate its stability. At this time, over 500 different miRNAs have been identified in human cells and evidence indicates that regulation of miRNA levels is associated with growth and differentiation of many cell types and tissues. Dysregulated miRNA expression has been associated with solid and hematopoietic malignancies, and there is evidence that some miRNAs may function as oncogenes or tumor suppressor genes. miR-221 and miR-222 are among the most deregulated miRNAs implicated in cancer. Their expression is highly upregulated in a variety of solid tumors, including thyroid cancer, hepatocarcinoma and melanoma cells. Elevated miR-221 and miR-222 expression has been causally linked to proliferation, apoptosis, and migration of several cancer cell lines. However, the molecular mechanisms mediating miR-221 and miR-222 function in cancer generally, and in NSCLC and HCC specifically, is largely unknown prior to the present invention.

PTEN is a tumor suppressor in human cancers and a regulator of cell growth and apoptosis. Functionally, PTEN converts phosphatidylinositol-3,4,5-trisphosphate (PIP3) in the cytoplasm to phosphatidylinositol-4,5-bisphosphate (PIP2), thereby directly antagonizing the activity of PI3 kinase (PI3K). PTEN inactivation results in constitutive activation of the PI3K/AKT pathway and in subsequent increase in protein synthesis, cell cycle progression, migration and survival. In addition, various studies have demonstrated that the protein phosphatase activity of PTEN inhibits activation of mitogen-activated protein kinase (MAPK) via several pathways. PTEN is associated with the development of multiple drug resistance, including that to TRAIL. Constitutive activation of AKT contributes to cell migration and invasion in different types of tumors, including lung and liver carcinoma.

TIMP3 is a member of a group of proteins called matrix metalloproteinases (MMPs). MMPs are a family of zinc proteases involved in the breakdown of extracellular matrix (ECM) in normal physiological processes, such as embryonic development, tissue and bone remodeling, wound healing, and angiogenesis. Within the extracellular matrix, the tissue inhibitors of metalloproteinases (TIMPs), of which there are four family members (TIMP1 through 4), inhibit the activity of MMPs by binding with a 1:1 stoichiometry to the active site. Over-expression of TIMP3 in vascular smooth muscle cells and melanoma cell lines inhibits invasion and promotes apoptotic cell death. TIMP3, has been reported to induce the activation of both initiator caspases-8 and -9. TIMP3 has been associated with angiogenesis and tumor formation.

MET, also known as c-Met, is a membrane receptor for the hepatocyte growth factor (HGF)/scatter factor (SF). MET is normally expressed by cells of epithelial origin, while expression of HGF is restricted to cells of mesenchymal origin. Upon HGF stimulation, MET stimulates the invasive growth of cancer cells and increases their metastatic potential, principally through increased phosphorylation of ERK1/2 and JNK.

Phosphorylated JNKs activate the oncoprotein, c-Jun, which is known to form the activator protein-1 (AP-1) transcription factor as a homodimer or heterodimer with its partner c-Fos. Aberrant expression of HGF/SF and its receptor, MET, often correlates with poor prognosis in a variety of human malignancies. Due to their specific toxicity for malignant cells, recombinant forms of TRAIL are apoptosis-based anti-tumor agents. However, many human cancer cells remain resistant to TRAIL-induced apoptosis, but the mechanism of such resistance is not clear.

SUMMARY OF THE INVENTION

The present invention provides methods to alter the TRAIL Expression Pattern in a cell, comprising inhibiting c-Jun, miR-221 and miR-222, PTEN or TIMP3 in a cell capable of expressing c-Jun, miR-221 and miR-222, PTEN and TIMP3, and observing a TRAIL Expression Pattern alteration.

Also provided are methods to alter the TRAIL Expression Pattern in a cell, comprising overexpressing c-Jun, miR-221 and miR-222, PTEN or TIMP3 in a cell capable of expressing c-Jun, miR-221 and miR-222, PTEN and TIMP3, and observing a TRAIL Expression Pattern alteration.

Also provided are methods to identify the TRAIL Expression Pattern in a cell sample, comprising identifying expression levels of at least two nucleic acids in a cell sample, wherein the at least two are selected from the group consisting of: miR-221 and miR-222 and c-Jun; miR-221 and miR-222 and PTEN; miR-221, miR-222 and TIMP3; miR-221 and miR-222, c-Jun and PTEN; miR-221 and miR-222, PTEN and TIMP3; and miR-221 and miR-222, c-Jun and TIMP3.

Also provided are methods to alter gene expression in a TRAIL resistant cell, comprising inhibiting miR-221 and miR-222 in a cell that also expresses at least one nucleic acid selected from the group consisting of: c-Jun; PTEN and TIMP3.

Also provided are methods to alter gene expression in a TRAIL resistant cell, comprising over-expressing miR-221 and miR-222 in a cell that also expresses at least one nucleic acid selected from the group consisting of: c-Jun; PTEN and TIMP3.

Also provided are methods to identify test cells having nucleic acid expression inhibition, comprising contacting at least one test cell with antisense miR-221 and miR-222 and observing an increase in expression of a nucleic acid selected from the group consisting of: PTEN and TIMP3.

Also provided are methods of predicting the clinical outcome of a patient diagnosed with cancer, comprising detecting the expression level of miR-221 and miR-222 and at least one nucleic expression level of a nucleic acid selected from the group consisting of: c-Jun; PTEN and TIMP3, in a cancer cell sample obtained from the patient, wherein a 1.5-fold or greater increase in the level of miR-221 and miR-222 in combination with a 1.5-fold or greater decrease in the level of PTEN or TIMP3 expression in the tumor sample relative to a control predicts a decrease in survival, or wherein a 1.5-fold or greater increase in the level of miR-221 and miR-222 in combination with a 1.5-fold or greater increase in the level of c-Jun expression in the tumor sample relative to a control predicts a decrease in survival.

Furthermore, the present invention also provides methods to inhibit down-regulation of PTEN expression in a tumor cell that expresses miR-221 and miR-222 and PTEN, comprising inhibiting miR-221 and miR-222 activity in a tumor cell that expresses miR-221 and miR-222 and PTEN and observing PTEN down-regulation inhibition. Preferred are methods as described, wherein said miR-221 and miR-222 activity is inhibited via antisense miR-221 and miR-222, although those wherein PTEN expression down-regulation inhibition is observed via TRAIL sensitivity are also preferred, as are methods wherein PTEN expression down-regulation inhibition is observed via PTEN transcription analysis.

In other embodiments, there are provided methods to identify a therapeutic agent for the treatment of TRAIL-resistant cancer, comprising screening candidate agents in vitro to select an agent that decreases expression of miR-221 and miR-222 and increases expression of PTEN in a TRAIL-resistant cancer cell, thereby identifying an agent for the treatment of TRAIL-resistance cancer.

Also provided are methods of treating a mammal having TRAIL-resistant tumor cells, comprising administering to mammal having TRAIL-resistant tumor cells as identified by a 1.5-fold or greater increase in the level of miR-221 and miR-222 in combination with a 1.5-fold or greater decrease in the level of PTEN expression, a therapeutic agent capable of inhibiting down-regulation of PTEN expression.

Also provided are kits for identifying miR-221 and miR-222 up-regulation of PTEN in test cells, comprising at least one molecular identifier of miR-221 and miR-222 and at least one molecular identifier of PTEN, wherein said molecular identifier is selected from the group consisting of: probes; primers; antibodies; or small molecule.

In any of the methods herein, the preferred method utilizes cells selected from the group consisting of: cancer cell; TRAIL-resistant cancer cell; non-small cell lung carcinoma; and HCC.

In yet another aspect of the present invention, there are provided methods to alter regulation of TIMP3 expression in a cell capable of expressing TIMP3 and miR-221 and miR-222, comprising altering miR-221 and miR-222 activity in a TIMP3-expressing and miR-221 and miR-222-expressing cell and observing TIMP3 expression alteration.

Also provided are methods to inhibit TIMP3 expression in a cell capable of expressing TIMP3, comprising over-expressing miR-221 and miR-222 in a cell that also expresses TIMP3 and observing TIMP3 expression inhibition.

Also provided are methods to identify cells having TIMP3 expression inhibition, comprising contacting a test cell with antisense miR-221& miR-222 and observing an increase in TIMP3 expression.

Also provided are methods to identify TRAIL-resistant cells, comprising identifying whether a test cell sample comprises miR-221 and miR-222 nucleic acid and TIMP3 nucleic acid.

Also provided are methods to identify a therapeutic agent for the treatment of TRAIL-resistant cancer, comprising screening candidate agents in vitro to select an agent that decreases expression of miR-221 and miR-222 and increases expression of TIMP3 in a TRAIL-resistant cancer cell, thereby identifying an agent for the treatment of TRAIL-resistance cancer.

Also provided are methods of predicting the clinical outcome of a patient diagnosed with cancer, comprising detecting the level of miR-221, miR-222 and TIMP3 expression in a cancer cell sample obtained from the patient, wherein a 1.5-fold or greater increase in the level of miR-221 and miR-222 in combination with a 1.5-fold or greater decrease in the level of TIMP3 expression in the tumor sample relative to a control predicts a decrease in survival.

Also provided are methods of treating a mammal with TRAIL-resistant tumor cells, comprising administering to mammal having TRAIL-resistant tumor cells as identified by a 1.5-fold or greater increase in the level of miR-221 and miR-222 in combination with a 1.5-fold or greater decrease in the level of TIMP3 expression, a therapeutic agent capable of inhibiting down-regulation of TIMP3 expression.

Also provided are kits for identifying miR-221& miR-222 upregulation of TIMP3 in test cells, comprising at least one molecular identifier of miR-221 and miR-222 and at least one molecular identifier of TIMP3, wherein said molecular identifier is selected from the group consisting of: probes; primers; antibodies; or small molecule.

Also provided are methods preferred methods, wherein said cell is selected from the group consisting of: cancer cell; TRAIL-resistant cancer cell; non-small cell lung carcinoma; and hepatocarcinoma.

Also provided are methods to inhibit down-regulation of TIMP3 expression in a tumor cell that expresses miR-221, miR-222 and TIMP3, comprising inhibiting miR-221 and miR-222 activity in a tumor cell that expresses miR-221, miR-222 and TIMP3 and observing TIMP3 down-regulation inhibition. Preferred are those methods as described, wherein said miR-221 and miR-222 activity is inhibited via antisense miR-221 and miR-222, or wherein TIMP3 expression down-regulation inhibition is observed via TRAIL sensitivity, or wherein TIMP3 expression down-regulation inhibition is observed via TIMP3 translation analysis.

The foregoing and other features and advantages of the disclosure will become more apparent from the following detailed description of several embodiments which proceeds with reference to the accompanying figures.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A. PTEN and TIMP3 3'UTRs contain one predicted miR-221 and miR-222 binding site. In FIG. 1A is shown the alignment of the seed regions of miR-221 & 222 with PTEN and TIMP3 3'UTRs. The sites of target mutagenesis are indicated in red. (FIG. 1A discloses SEQ ID NOS 26-29, and 26, 30, 28, and 31, respectively, in order of appearance.)

FIG. 1B. qRT-PCR in MEG01 cells after enforced expression of miR-221 and miR-222.

FIG. 1C. PTEN and TIMP3 3' UTRs are targets of miR-221 and miR-222. pGL3-PTEN and pGL3-TIMP3 luciferase constructs, containing a wild type (left side of the histograms) or mutated (right side of the histograms) PTEN and TIMP3 3' UTRs, were transfected into MEG01 cells. Relative repression of firefly luciferase expression was standardized to a transfection control. The reporter assays were performed three times with essentially identical results.

FIG. 1D. qRT-PCR in H460 cells after enforced expression of miR-221 and miR-222.

FIG. 1E. miR-221 and miR-222 enforced expression decreases endogenous levels of PTEN and TIMP3 proteins in H460 NSCLC. H460 cells were transfected with either scrambled or miR-221 or miR-222 for 72 h. PTEN and TIMP3 expression was assessed by western blot. Loading control was obtained by using anti-β-actin antibody.

FIG. 1F. qRT-PCR showing miR-221 and miR-222 down-modulation in Calu-1 cells after anti-miRs transfection.

FIG. 1G. Western blot showing PTEN and TIMP3 expression after miR-221 and miR-222 downregulation by using anti-miR-221 and miR-222. Anti-miR-221 and -222 were able to increase PTEN and TIMP3 expression in Calu-1 cell line.

FIG. 1H. qRT-PCR of PTEN and TIMP3 mRNA after miR-221 and miR-222 forced expression in H460 cells. PTEN but not TIMP3 mRNA was downregulated by miR-221 and miR-222. Data are presented as SD.

FIG. 2A. miR-221 and -222 expression levels was assessed by northern blot analysis using 15 μg of total RNA for NSCLC and 10 μg of total RNA for HCC cells. Western Blots anti-PTEN and TIMP3 were performed using total proteins extract (50 μg) isolated from the different NSCLC and HCC.

FIG. 2B. qRT-PCR of miR-221 and miR-222 and PTEN mRNA was performed by extracting RNA from the different NSCLC and HCC as described in the "Supplemental Experimental Procedures" section. miR-221 and miR-222 were inversely related to PTEN mRNA expression in all the different NSCLC and HCC cells. Data are presented as SD.

FIG. 3A. Western blot showing PTEN and TIMP3 expression in Sk-Hep1 and Snu-387 cells after miR-221 and miR-222 overexpression or downregulation. miR-221 and miR-222 were able to downregulate PTEN and TIMP3 expression in Sk-Hep1; conversely, anti-miR-221 and miR-222 were able to increase PTEN and TIMP3 expression in Snu-387 cells.

FIG. 3B. qRT-PCR on 22 lung cancer patients and 10 normal lung tissues. The association between miR-221/miR-222 and PTEN mRNA for the 10 subjects in the normal class and for the 22 subjects in the tumor class was calculated statistically by using the Pearson Correlation Coefficient (r) and the respective p-value, all significant at p0.05. The Pearson correlation indicated an inverse relation between miR-221,-222 and PTEN mRNA in the normal and tumor samples.

FIG. 3C. IHC and ISH on hepatocarcinoma and normal liver tissues samples. miR-221/miR-222 (blue) and PTEN/TIMP3 (red) expression were inversely related in liver cancers and the adjacent normal/cirrhotic liver tissues. These tissues were analyzed for miR-221 and miR-222 expression by in situ hybridization, followed by immunohistochemistry for PTEN and TIMP3. Liver cancer cells abundantly expressed miR-221/miR-222 and rarely expressed PTEN or TIMP3 (labeled as G, H, K, L) whereas the adjacent non-malignant liver abundantly expressed PTEN or TIMP3 and rarely had detectable miR-221/miR-222 (labeled as A, B, E, F). In the cases of hepatocellular carcinoma where both miR-221/miR-222 and TIMP3 expression were noted, the cancer cells expressing miR-221 (large arrow, labeled as K; TIMP3 is depicted by arrow in labeled as L) were distinct from those cells expressing TIMP3 (labeled as K, small arrow). Labeled as C-I, H & E; D-J miR-302, which is not express in liver, was used as negative control. 80 human HCC were analyzed. Scale bars indicate 25 m.

FIG. 4A. Proliferation assay on five different HCC. Cells were incubated with Super-Killer-TRAIL (400 ng/ml) for 24 h and viability evaluated as described in the supplemental methods. Huh7, HepG2 and Sk-Hep1 with low miR-221 and -222 expression, were more sensitive to TRAIL-induced apoptosis compared to PLC/PLF-5 and Snu-387, highly expressing miR-221/miR-222. Mean SD of four independent experiments repeated in triplicate.

FIG. 4B. Cell death effects in Sk-Hep1 cells after miR-221/miR-222 forced expression and PTEN or TIMP3 downregulation. Cells were transfected either with control miR or with pre-miR-221-222. 24 h after transfection, cells were treated with Super-Killer TRAIL for 24 hours. Apoptosis was evaluated either with Annexin-FITC or (FIG. 4C) with caspase-Glo 3/7 kit. TRAIL resistance increased after miR-221/miR-222 overexpression or PTEN and TIMP3 downmodulation.

FIG. 4D. Effects of miR-221/miR-222 on cell death. H460 cells were transfected either with control siRNA or control miR or with 100 nmol of PTEN and TIMP3 siRNA. After 48 h from the transfection cells were treated with Super-Killer TRAIL for 24 hours. Apoptosis was evaluated by caspase 3/7 activity or FIG. 4E) Annexin-V. Percentage of apoptotic cells decreased after PTEN and TIMP3 downregulation. Error bars indicate SD. *p<0.05, **p<0.001 by t test.

FIGS. 5A-5G. Anti-miR-221 and miR-222 override TRAIL-resistance in NSCLC and HCC through the inhibition of the AKT pathway.

(FIGS. 5A-5C) Western Blots in H460 cells after miR-221/miR-222 forced expression. miR-221 and miR-222 forced expression induces the activation of the AKT/ERKs pathways and Metallopeptidases.

FIG. 5B. Western blots in Snu-387 cells after miR-221 and miR-222 knockdown by anti-miR-221/miR-222. The inhibition of the AKT pathway is showed as result of miR-221 and miR-222 downregulation.

FIGS. 5D-5E. Western blots after PTEN or TIMP3 knockdown. Erks phosphorylation and PAK1 activation are both PTEN and TIMP3 dependent. The activation of the AKT pathway is PTEN-dependent, while TIMP3 silencing induces the expression of metallopeptidases.

FIG. 5F-5G. Effects of anti-miRs and AKT pathway inhibition by API2/triciribine on cell death. Calu-1 and Snu-387 cells were transfected with anti-miR221/miR-222 for 72 h, or treated with API2/triciribine for 48 h. miR-221 and miR-222 downmodulation and/or the inhibition of the Akt pathway, induced an increase in apoptosis percentage in both Calu-1 and Snu-387 cell lines, as assessed by caspase 3/7 activity. Error bars indicate SD. **$p<0.001$ by t test.

FIG. 6A. Flow cytometric distributions of H460 cells transfected with pre-miR scrambled, miR-221 and miR-222, siRNA scrambled, siRNA PTEN. H460 transfected cells showed a decrease of G1 and a corresponding increase of the S and G2-M phases, as a consequence of PTEN downregulation.

FIGS. 6B-6C. miR-221 and miR-222 regulate cell migration ability in H460 cells. Migration Assay was performed as described in the "Experimental Procedures".

FIG. 6D. miR-221 and miR-222 influences H460 and Sk-Hep1 cell invasion ability. Histogram reports the percentage of cells that invaded through Matrigel-coated membrane after transfection with negative control miRNA, miR-221, miR-222, siPTEN and siTIMP3. One-way analysis of variance (ANOVA) was performed to test the differences among means of invasion values. The Scheffe' multiple-comparison method was used to test the differences between each pair of means. Significant differences were found between the scrambled vs miR-221 and miR-222, PTEN and TIMP3 H460 transfected cells (p-value 0.001). The same results were obtained using the Bonferroniii and Sidak methods. Error bars indicate SD. *$p<0.001$ by t test. Scale bar indicates 25 m. The magnification is the same for all the panels.

FIGS. 7A-7K. MET oncogene regulates miR-221 and miR-222 activation.

(FIGS. 7A-7B-7C). Relative expression levels of miR-221 and miR-222 in Calu-1, Snu-387 and GTL16 after transfection with miR control and siRNA MET. miR-221 and miR-222 expression decreased after MET knockdown.

FIGS. 7D-7E-7F. Western blots after siRNA MET transfection in Calu-1, Snu-387 and GTL16 cells. MET knockdown decreased miR-221 and miR-222 expression levels, giving rise to PTEN and TIMP3 upregulation in all the different cell lines. GTL16 cells were moreover treated for 24 h with 4 µM of the MET inhibitor SU11274. MET inhibition increased miR-221 and miR-222 targets expression levels.

FIGS. 7G-7H-7I. Identification of c-Jun (AP-1) interacting region by using 2 different amplicons across the miR-221/miR-222 transcription start site. ChIP analysis was performed with chromatin from H460 c-Jun negative cells, Calu-1 and Snu-387 c-Jun positive cells. BS=binding site.

FIG. 7J. qRT-PCR of miR-221 and miR-222 in Huh7 cells after treatment with anisomycin (10 M) for 30 min Anisomycin induced miR-221 and miR-222 upregulation.

FIG. 7K. Anisomycin induced c-Jun activation and PTEN and TIMP3 downregulation in Huh7 cells. Total lysate was analyzed by western blot using anti-PTEN and anti-TIMP3 antibody. Error bars indicate SD.

FIG. 8. MET induces miR-221 and miR-222 activation through AP-1 (c-Jun) transcription factor. A model is reported in which growth factors determine c-Met activation which, in turn, through AP-1 and accordingly miR-221 and miR-222 upregulation, gives rise to PTEN and TIMP3 downregulation and subsequent apoptosis resistance, cellular migration and invasion.

FIGS. 9C-9H. H&E—Small arrow miR-221-222, big arrow TIMP3. 92 human lung carcinomas were analyzed.

FIGS. 9K-9L. Correlation of miRNA-221/miR-222 expression and histology in the lung. miR-221 and -222 showed equivalent distribution patterns in this squamous cell carcinoma of the lung. FIG. 9K shows a strong signal (large arrow) in the nests of tumor cells that are infiltrating the adjacent fibrotic lung tissue. Note that the signal shows a cytoplasmic and nuclear membrane based localization in the cancer cells (FIG. 9L, higher magnification). In comparison, only rare benign cells express miR-222 in the adjacent fibrotic tissue (small arrow) which is being invaded by the cancer cells. Scale bars indicate 25 m.

FIG. 11A. Caspase 3/7 activity in Calu-1 cells after PTEN, TIMP3 and PTEN/TIMP3 upregulation. Cells were cultured in 96-well plates, transfected with PTEN, TIMP3 or both for 72 h. After 48 h from transfection cells were treated with TRAIL 400 ng/ml for 24 h and analyzed using Caspase-Glo 3/7 Assay kit according to the manufacturer's instructions. Calu-1 cells became sensitive to TRAIL-inducing apoptosis after PTEN, TIMP3 or both PTEN/TIMP3 overexpression.

FIG. 11B. Effects of PTEN and TIMP3 on cell death. Calu-1 cells were transfected either with PTEN and TIMP3 plasmids. After 48 h from the transfection cells were treated with 400 ng/ml of Super-Killer TRAIL for 24 hours. Apoptosis was evaluated by Annexin-V. Percentage of apoptotic cells increases after PTEN and TIMP3 upregulation.

Figure 11A:
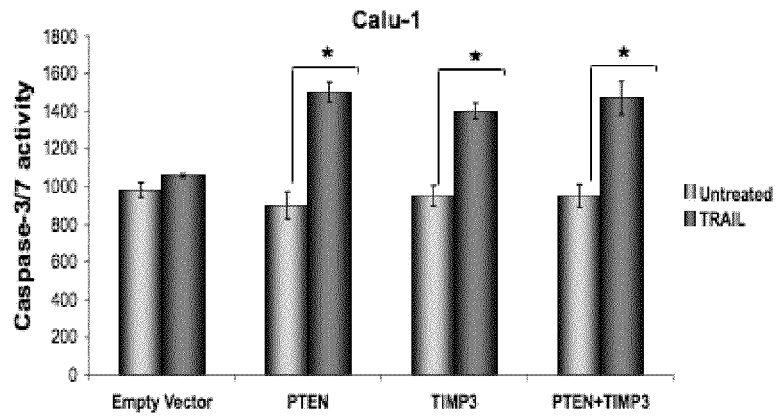
FIGS. 11A-11C. TIMP3 overexpression induces apoptosis in Calu-1 TRAIL resistant cells.
Figure 11B:
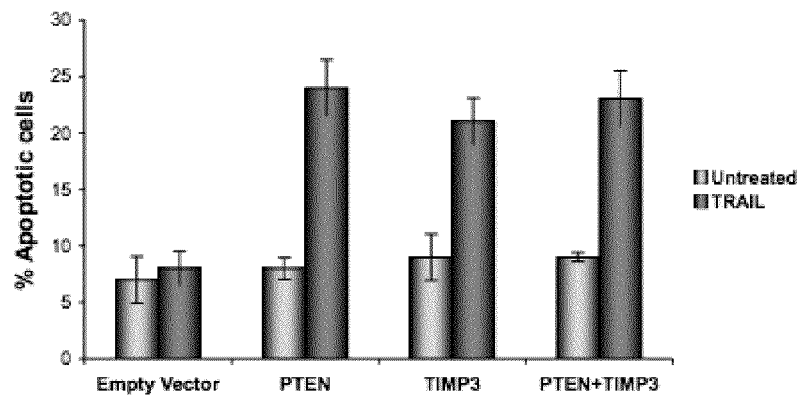
Figure 11C:
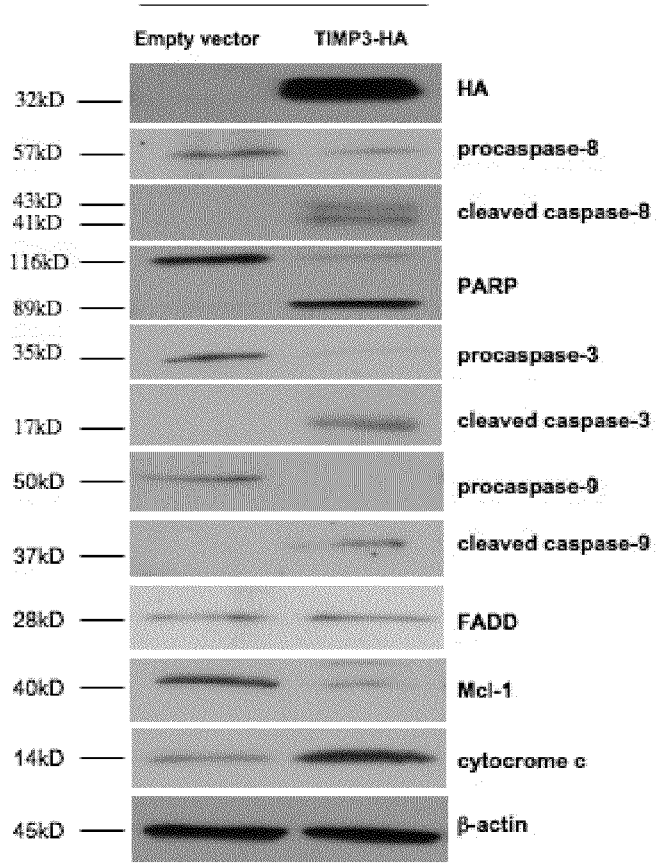

FIG. 11C. Western Blots in Calu-1 cells after TIMP3 overexpression. Fifty micrograms of total extract was loaded onto SDS-PAGE polyacrylamide gels and membranes were blotted with the indicated antibodies. TIMP3 overexpression activates both the extrinsic and intrinsic apoptotic pathways. Error bars indicate SD. *p<0.001 by t test.

FIGS. 12A-12G. Effects of PTEN and TIMP3 silencing on tumorigenicity of H460 cells in vivo.

Figure 12A:
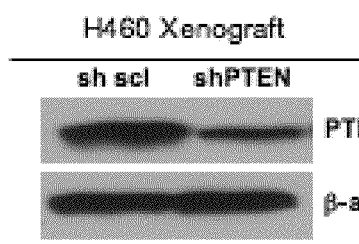
Figure 12B:
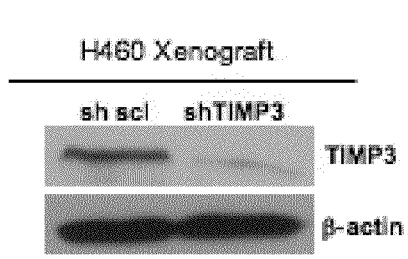

FIG. 12A-12B. Western blots showing PTEN and TIMP3 expression in H460 xenografts after shPTEN and shTIMP3 stable transfection. 35 days from the injection mice were sacrificed and tumors were analyzed by western blot.

Figure 12C:
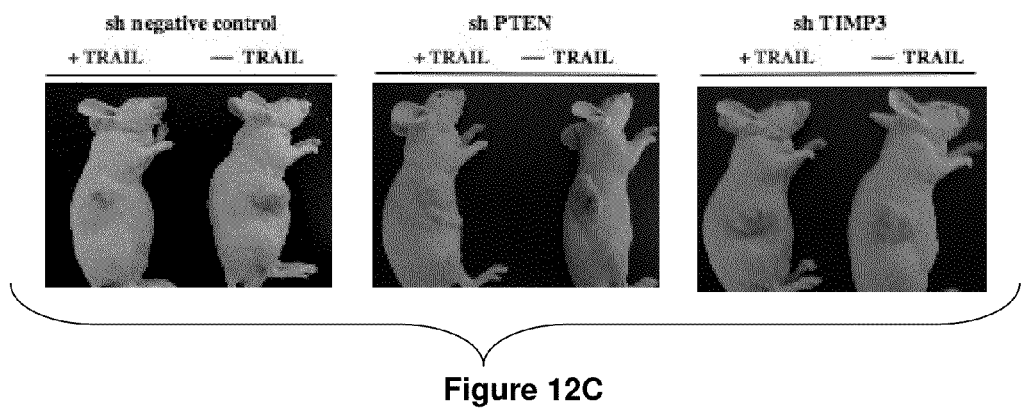
Figure 12D:
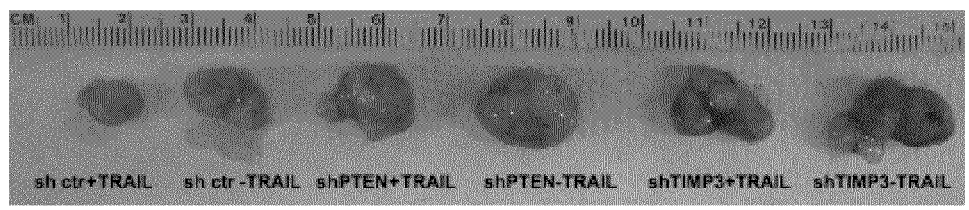

FIG. 12C-12D. Comparison of tumor engraftment sizes of sh control, shPTEN and shTIMP3 in H460 cells 35 days from the injection in nude mice and after treatment with vehicle (PBS) or TRAIL. PTEN and TIMP3 knockdown increases TRAIL resistance in vivo. The images show average-sized tumors from among five of each category.

Figure 12E:
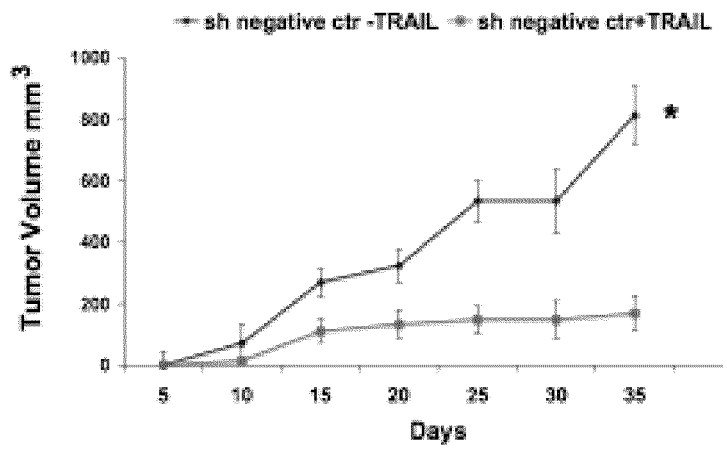
Figure 12F:
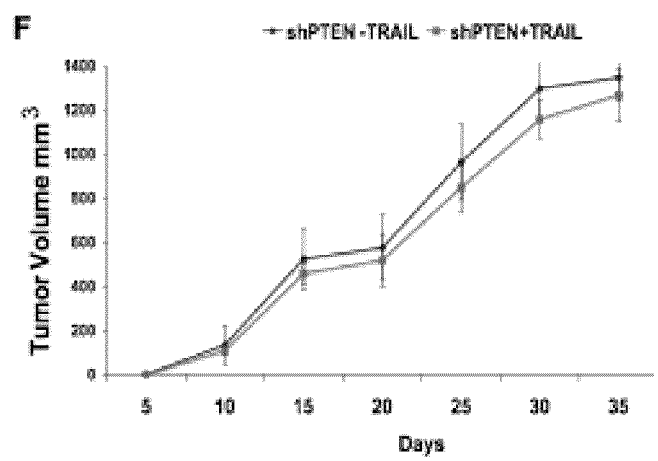
Figure 12G:
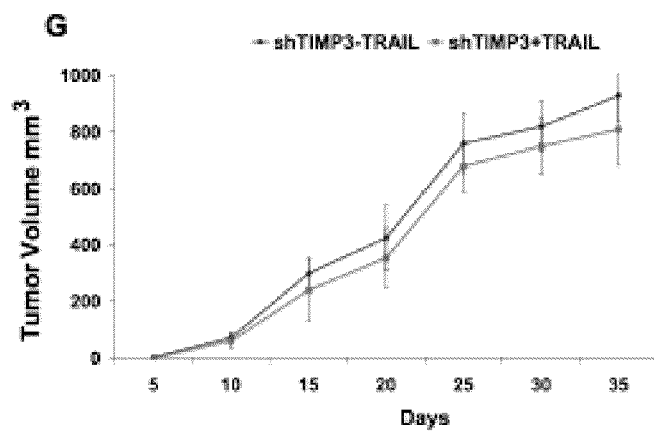

FIGS. 12E-12F-12G. Growth curve of engrafted tumors in nude mice injected with H460 cells stable transfected with sh control, sh PTEN and shTIMP3. Data are presented as SD. *p 0.001.

Figure 13A:
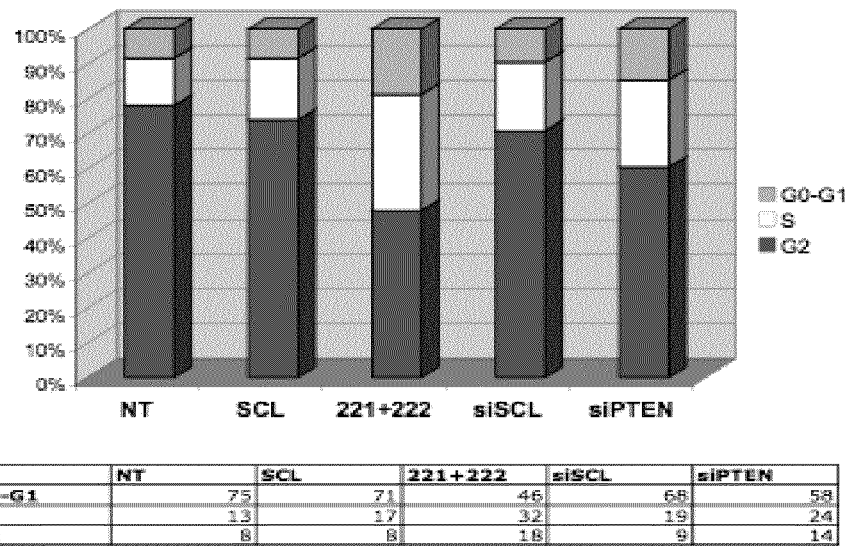
Figure 13B:
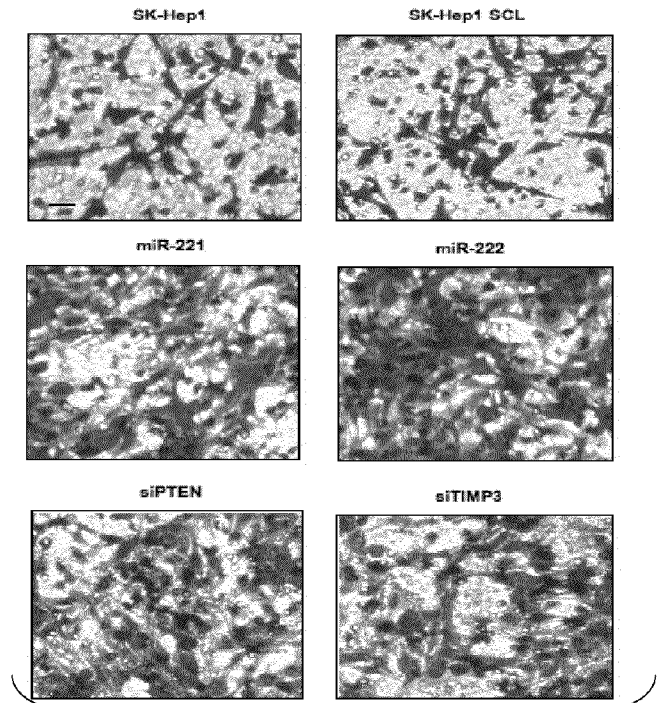

FIGS. 13A-13B. Ectopic expression of miR-221 and miR-222 affects the cell cycle distribution and migration/invasion capabilities of Sk-Hep1 cells.

FIG. 13A. Flow cytometric distributions of Sk-Hep1 cells transfected with empty vector, miR-221 and miR-222, siRNA PTEN. The average of three independent experiments is reported.

FIG. 13B. miR-221 and miR-222 regulate cell migration ability in Sk-Hep1 cells. Transwell insert chambers with 8-nm porous membrane were used for the assay. After transfection cells were washed with PBS and 150,000 cells were added to the top chamber in serum-free media. The bottom chamber was filled with media containing 10% FBS. To quantify migrating cells, cells on the top chamber were removed by using a cotton-tipped swab, and the migrated cells were fixed in PBS, 25% glutaraldehyde and stained with Crystal Violet stain. Four random fields were counted. Scale bar indicates 25 m. The magnification is the same for all the panels.

Figure 14A:
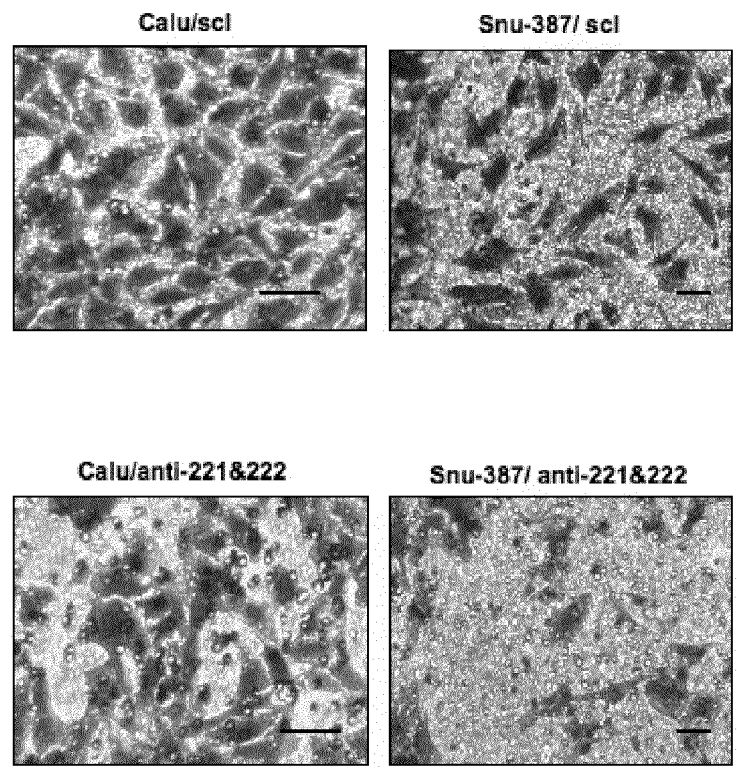
Figure 14B:
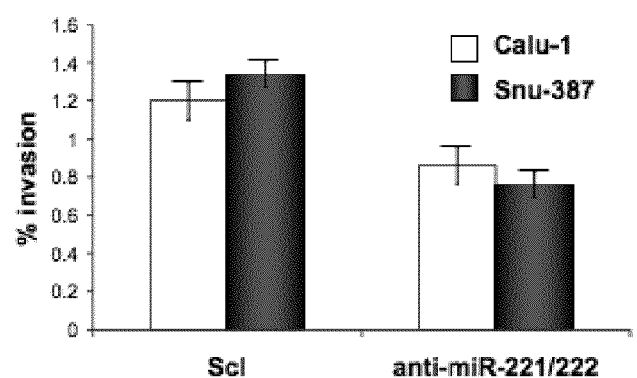

FIGS. 14A-14B. 2'-O-me-anti-mR-221 and miR-222 reduce cell migration and invasion ability of Calu-1 and Snu-387 cells.

FIG. 14A. Transwell insert chambers with 8 μm porous membrane were used for the assay. After transfection cells were washed with PBS and 50,000 cells were added to the top chamber in serum-free media. The bottom chamber was filled with media containing 10% FBS. To quantify migrating cells, cells on the top chamber were removed by using a cotton-tipped swab, and the migrated cells were fixed in PBS, 25% glutaraldehyde and stained with Crystal Violet stain. Five random fields were counted. miR-221 and miR-222 knockdown reduce Calu-1 and Snu-387 cells migration.

FIG. 14B. miR-221 and miR-222 influence Calu-1 and Snu-387 cell invasion ability. Histogram reports the percentage of cells that invaded through Matrigel-coated membrane after transfection with negative control miRNA, anti-miR-221, or anti-miR-222. Data are presented as ±SD of 3 separate determinations. Scale bars indicate 25 m.

FIGS. 15A-15F. c-Jun binds to miR-221/miR-222 promoter determining its activation.

Figure 15A:
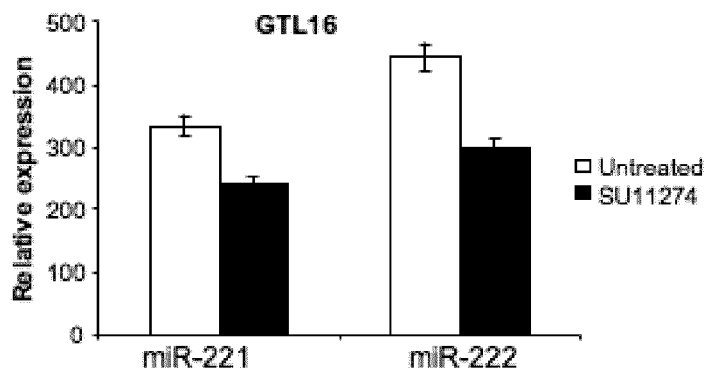

FIG. 15A. qRT-PCR in GTL-16 cells after MET inhibition by using the MET inhibitor SU11274. miR-221 and miR-222 were downregulated of about 40%, as compared with the untreated cells.

Figure 15B:
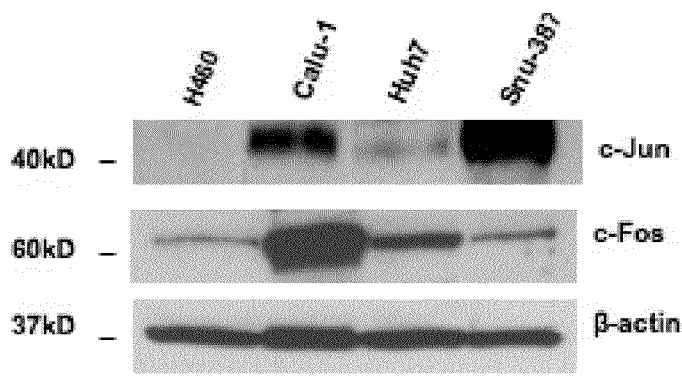

FIG. 15B. c-Jun and c Fos expression levels in four different cell lines. 50 μg of total lysates were loaded onto a 12% polyacrylamide gel. Calu-1 and Snu-387 showed high c-Jun expression, Huh7 low expression levels and in H460 c-Jun expression was absent. c-Fos expression level is very high in Calu-1 cells, lower in all the other cell lines.

Figure 15C:
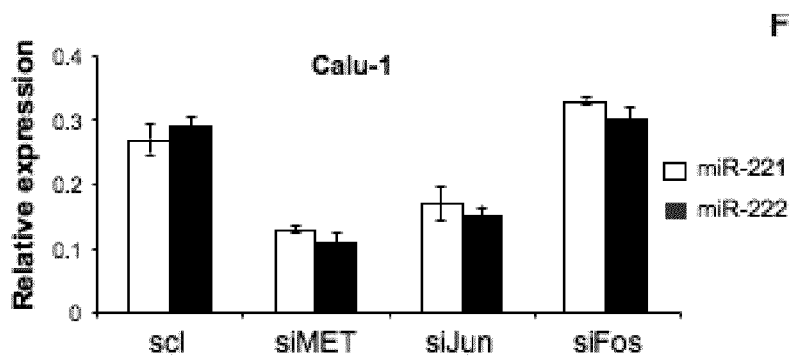

FIG. 15C. qRT-PCR on Calu-1 cells after MET, c-Jun, and c-Fos downregulation. Total 5 ng of RNA in 10 μl PCR was used. TaqMan ΔCT values were converted into absolute copy numbers using a standard curve from synthetic lin-4 miRNA. Data are expressed as the relative expression of the different miRs, compared to U44 and U48 rRNA. miR-221 and miR-222 are downregulated after MET and c-Jun but not c-Fos knockdown by siRNAs, demonstrating that c-Jun is the transcription factor responsible for miR-221 and miR-222 activation.

Figure 15D:
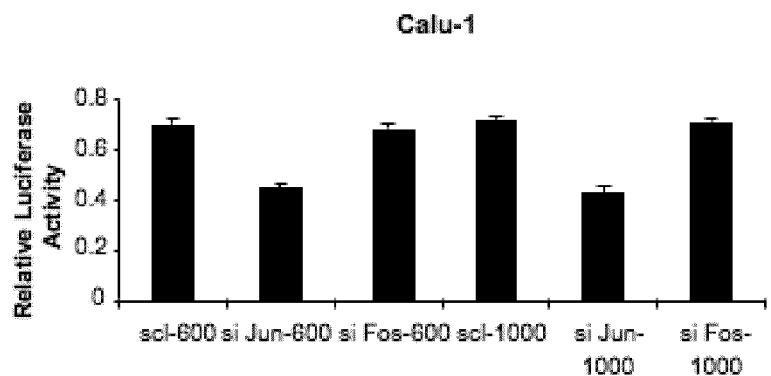
Figure 15E:
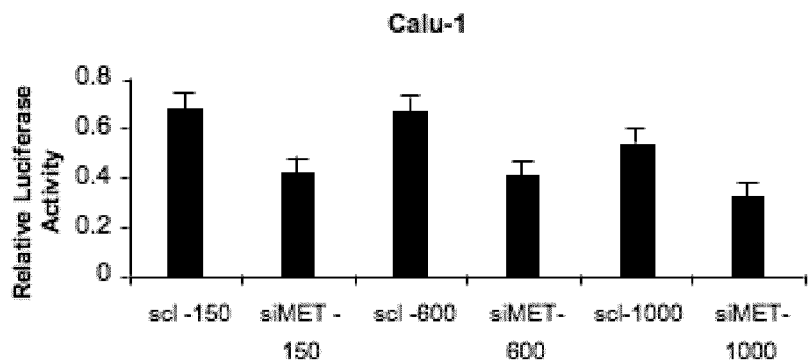

FIGS. 15D-15E. Luciferase assays in Calu-1 cells after cotransfection with reporter plasmid harboring different sites of miR-221 and miR-222 promoter (−150, −600, −1000) and siRNA MET, siRNA c-Jun, siRNA c-Fos. MET and c-Jun siRNAs but not c-Fos siRNA, were able to decrease miR-221 and miR-222 luciferase activity.

Figure 15F:
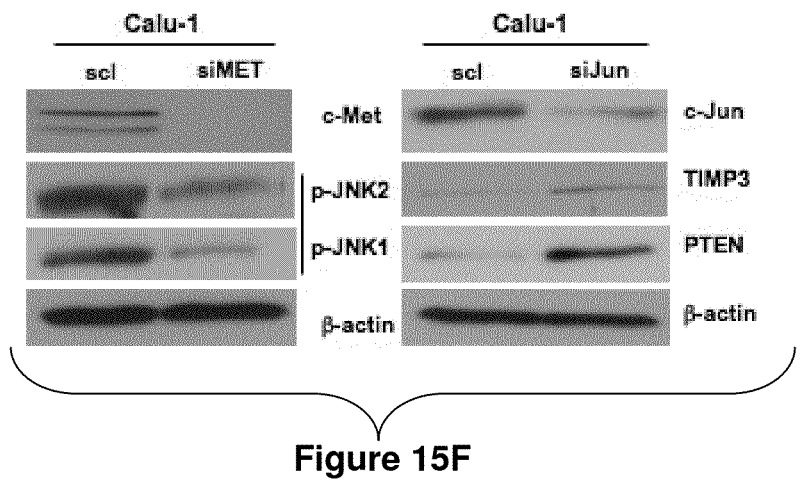

FIG. 15F. Western blots after c-Met and c-Jun silencing. MET knockdown reduces JNK1/2 phosphorylation. c-Jun silencing gives rise to an increased expression of PTEN and TIMP3. Data are presented as ±SD.

FIGS. 16A-16H. PTEN, TIMP3 and MET co-labeling. IHC and ISH were performed on 72 lung tumor samples.

Figures 16A, 16B, 16C, 16D, 16E, 16F, 16G, 16H:
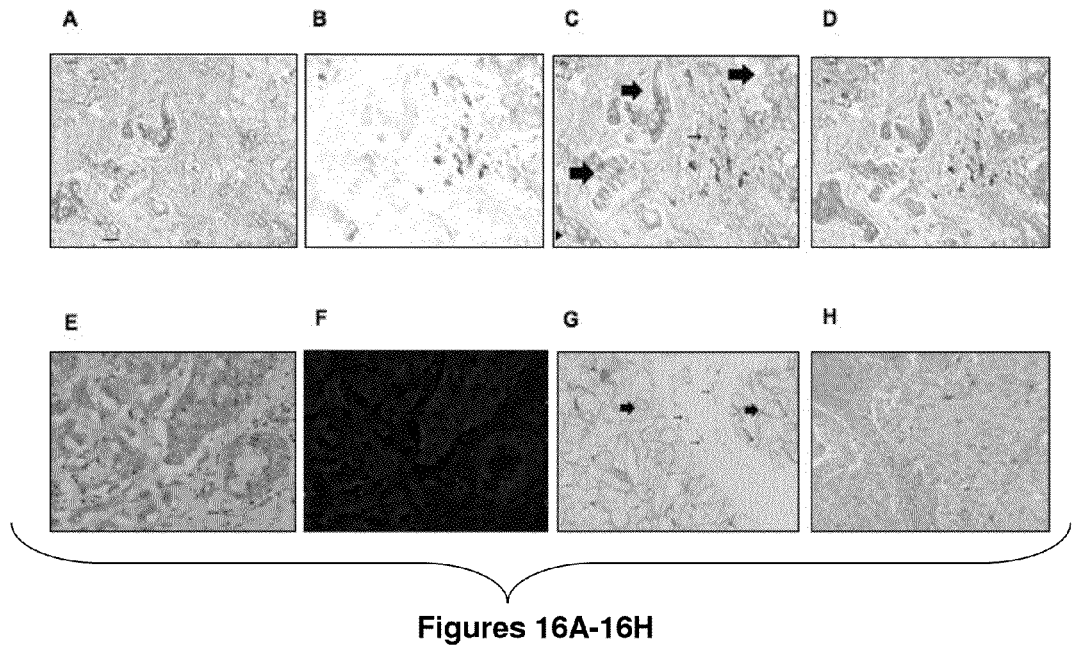

FIG. 16A. IHC of c-Met alone (brown).

FIG. 16B. TIMP3 alone (red).

FIG. 16C. c-Met/TIMP3 colabeling in lung cancers.

FIG. 16D. Nuclei as demonstrated by a hematoxylin counterstain. c-Met is expressed only in the cancer cells (big arrows) whereas TIMP3 is expressed in the surrounding benign cells (small arrows). Note that when c-MET is present TIMP3 is absent and vice versa.

FIG. 16E. Colocalization of c-Met (red) and TIMP3 (brown) in hepatocellular carcinoma (60 tumor samples were analyzed). Note that the tumor cells express c-Met and that TIMP3 expression is not evident. The panel also shows the hematoxylin stained features of the cancer, marked by multiple invasive nests in a desmoplastic stroma.

FIG. 16F. The same field analyzed by the Nuance system, with fluorescent red representing c-Met, fluorescent yellow representing TIMP3, and fluorescent green cells co-labeled with c-Met and TIMP3. As evident, no cancer cells co-label with c-Met and TIMP3.

FIG. 16G. Colocalization of c-Met and PTEN in lung carcinoma. The c-Met stain (red) shows the cell membrane pattern typical for c-Met in the cancer cells (large arrows). Adjacent to them is the stroma, with its benign fibroblasts and macrophages that express PTEN (brown-small arrow) but not cMET.

FIG. 16H. H&E—Scale bar indicates 25 m. The magnification is the same for all the panels.

FIG. 17A-17E. MET silencing reduces cell migration and invasion in Calu-1 and Snu-387 cells and enhances TRAIL sensitivity in vivo.

Figure 17A:
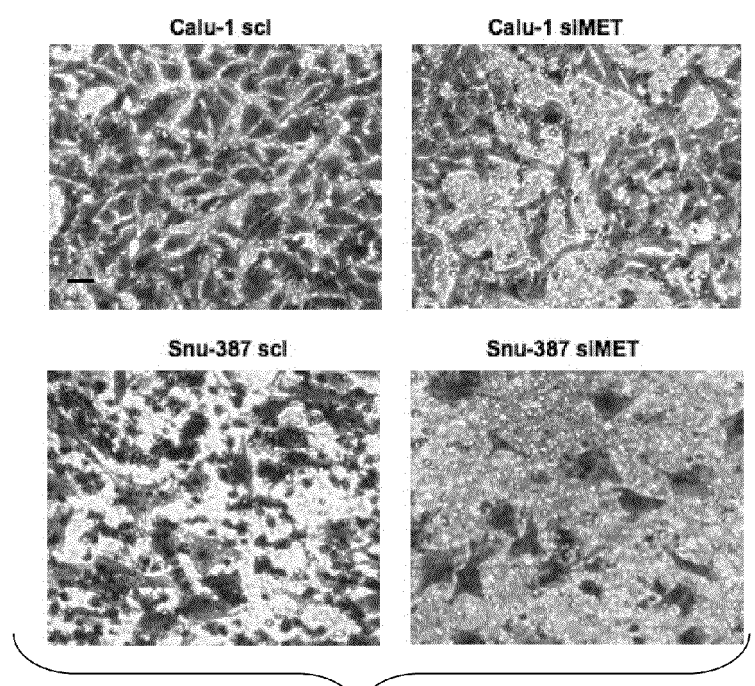

FIG. 17A. Transwell insert chambers with 8-nm porous membrane were used for migration assay. After transfection cells were washed with PBS and 50.000 cells were added to the top chamber in serum-free media. The bottom chamber was filled with media containing 10% FBS. To quantify migrating cells, cells on the top chamber were removed by using a cotton-tipped swab, and the migrated cells were fixed in PBS, 25% glutaraldehyde and stained with Crystal Violet stain. Five random fields were counted.

Figure 17B:
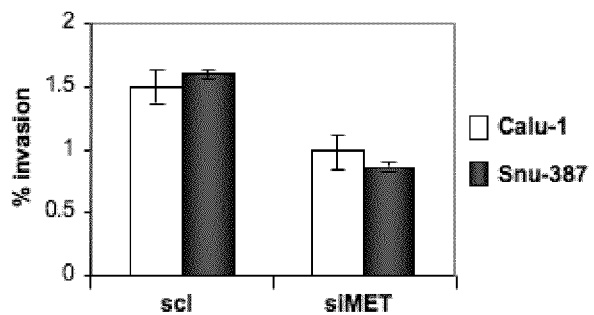

FIG. 17B. MET influences Calu-1 and Snu-387 cell invasion ability. Histogram reports the percentage of cells that invaded through Matrigel-coated membrane after transfection with siRNA negative control or siRNA MET. Data are expressed as mean±standard error of 3 separate determinations.

Figure 17C:
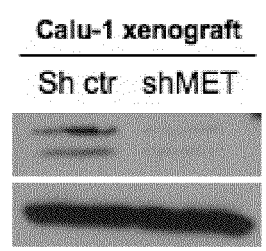

FIG. 17C. Western blots showing MET expression in Calu-1 xenografts after shMET stable transfection. 35 days from the injection mice were sacrificed and tumors were analyzed by western blot.

Figure 17D:
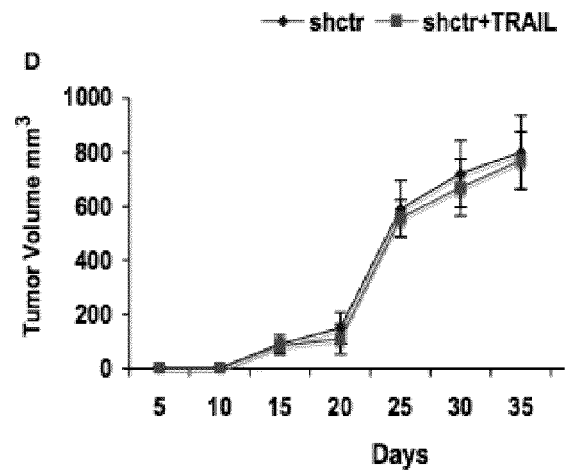
Figure 17E:
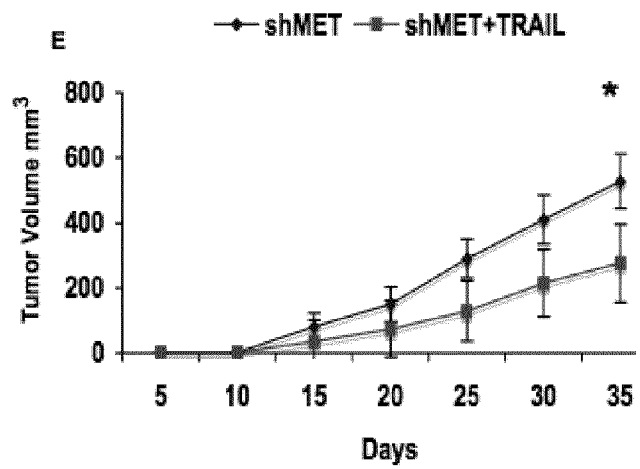

FIGS. 17D-17E. Growth curve of engrafted tumors in nude mice injected with Calu-1 cells stable transfected with sh control and shMET. Data are presented as SD. *p 0.01. Scale bar indicates 25 m. The magnification is the same for all the panels.

SEQUENCE LISTING

The instant application contains a Sequence Listing which has been submitted via EFS-web and is hereby incorporated by reference in its entirety. The ASCII copy, created on Nov. 22, 2010, is named 604__51413_SEQLIST_OSU-10076.txt, and is 7,374 bytes in size.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

The present invention provides that the activation of miR-221 and miR-222 is regulated, at least in part, by the MET oncogene and the c-Jun transcription factor, and which, in turn, down-regulates PTEN and TIMP3.

Activation of MET signaling is a frequent genetic event observed in liver and lung cancer development. AP-1 is a complex of dimeric basic region-leucine zipper proteins that belong to the Jun (c-Jun, JunB, JunD), Fos (c-Fos, FosB, Fra-1 and Fra-2), Maf and ATF subfamilies c-Jun is the most potent transcriptional activator in its group, whose transcriptional activity is attenuated and sometimes antagonized by JunB. The Fos proteins, which cannot homodimerize, form stable heterodimers with Jun proteins and thereby enhance their DNA binding activity.

The present inventors focused on these two AP-1 subfamilies, and in particular on c-Jun and c-Fos, although they found by bioinformatics search (TESS database) that also ATF-1 and JunD, could be potential transcription factors involved in miR-221 and miR-222 activation. The present invention demonstrates that c-Jun and not c-Fos is involved in miR-221 and miR-222 activation and that c-Jun has one binding site in the miR-221/miR-222 promoter region. The induction of AP-1 is mostly mediated by the JNK cascades.

By using anisomycin, an antibiotic which activates the JNK cascade, the inventors found an increase of miR-221/miR-222 expression in Huh7 hepatocarcinoma cells, as consequence of c-Jun phosphorylation. Intriguingly, when the inventors grew Huh7 cells in serum free medium, they did not observe any variation in the expression level of miR-221 and miR-222 or PTEN and TIMP3, showing that MET activation is important for miR-221 and miR-222 transcription regulation and subsequent cellular migration.

To address this issue the inventors investigated Calu-1 and Snu-387 cell migration and invasion after MET silencing. Migratory and invasive capabilities of both cell lines were reduced after MET oncogene silencing (FIGS. 17A-17B).

Furthermore, a xenograft model of Calu-1 cells in which c-Met was silenced by using an shMET plasmid (FIG. 17C), showed that mice injected with Calu-1 shMET cells are more sensitive to TRAIL inducing apoptosis compared to the mice injected with the sh control (FIGS. 17D-17E). Thus MET confers not only a tumor growth advantage but also resistance to TRAIL-inducing apoptosis over control tumors in vivo. Therefore, MET oncogene regulates miR-221 and miR-222 levels and, accordingly, cellular invasion and migration through c-Jun transcription factor and JNK activation (FIG. 8).

Taken together, these data highlight a mechanism, involving MET, through which miR-221 and miR-222 promote tumorigenesis and metastasis. Thus approaches targeting MET receptor and/or miR-221 and miR-222 in order to sensitize NSCLC and HCC to TRAIL-inducing apoptosis, but also in the prevention and inhibition of lung cancer and hepatocellular carcinoma, are included in the present invention.

In the present invention, there are identified major mRNA targets and signaling pathways that mediate miR-221 and miR-222 regulation in a wide panel of NSCLC and HCC-derived cell lines. In vitro and in vivo experiments reveal that elevated levels of miR-221 and miR-222 in NSCLCs and HCCs correlates with PTEN and TIMP3 down-regulation, indicating that these two microRNAs are a causal factor in the down-regulation of PTEN and TIMP3 in these types of cancers.

The inventors examined the effects of miR-221 and miR-222 and their targets on cell survival and TRAIL resistance. Interestingly, the inventors found that after miR-221/miR-222 enforced expression, or PTEN and TIMP3 down regulation, TRAIL-sensitive NSCLC and HCC cells became resistant to TRAIL-inducing apoptosis, although PTEN down regulation was slightly more effective than that of TIMP3.

The present invention provides methods to affect miR-221 and miR222 expression, since it is now proved that miR-221 and miR-222 expression is a "prerequisite" of TRAIL-resistant NSCLC and HCC cells. Importantly, tumor stratification, on the basis of miR-221/miR-222 expression levels, could be used as prognostic tool to predict TRAIL-sensitivity or TRAIL-resistance in the treatment of NSCLCs and HCCs.

The present invention also discloses that miR-221 and miR-222 block PTEN expression leading to activation of the AKT pathway, showing that miR-221 and miR-222 plays an important role in cell growth and invasiveness by targeting the PTEN/AKT pathway. In this regard, cell cycle analysis evidenced an increase in cell growth tightly linked to the G1 to S shift, which is in agreement with modulation of PTEN and also of p27kip1, a known regulator of the G1/S cell cycle checkpoint and a downstream effector of PTEN.

NSCLC and HCC cells overexpressing miR-221 and miR-222 are not only TRAIL-resistant but they also show an increase in migration and invasion capabilities, compared to cells expressing lower levels of miR-221 and miR-222 cells.

Moreover, miR-221 and miR-222 are herein shown to promote cell migration, invasion and growth via direct repression of PTEN and TIMP3 expression and of downstream pathways involving AKT and ERKs phosphorylation, and the activation of MMP-3 and MMP-9.

Further, PTEN and TIMP3 loss in H460 tumor xenograft conferred not only a significant tumor growth advantage but also a resistance to TRAIL-inducing apoptosis over control tumors also in vivo. Interestingly, the TIMP3 knockdown tumors were more vascularized than the control tumors, highlighting its role in angiogenesis and tumor formation.

The identification of miR-221 and miR-222 as important regulators of tumor cell proliferation, migration, and invasion of NSCLC and HCC, in vitro and in vivo, provides insights into the role of these miRNAs in hepatic and lung oncogenesis and tumor behavior.

The effects of miR-221 and miR-222 and their targets on cell survival and TRAIL resistance were examined. Interestingly, after miR-221/miR-222 enforced expression, or PTEN and TIMP3 downregulation, TRAIL-sensitive NSCLC and HCC cells became resistant to TRAIL-inducing apoptosis, although PTEN down regulation was slightly more effective than that of TIMP3. This indicates that miR-221 and miR-222 overexpression is a "prerequisite" of TRAIL-resistant NSCLC and HCC cells.

Importantly, tumor stratification, on the basis of miR-221/miR-222 expression levels, could be used as prognostic tool to predict TRAIL-sensitivity or TRAIL-resistance in the treatment of NSCLCs and HCCs.

ABBREVIATIONS

DNA Deoxyribonucleic acid
HCC Hepatocellular carcinoma
IL Interleukin
ISH In situ hybridization
miR MicroRNA
miRNA MicroRNA
mRNA Messenger RNA
PCR Polymerase chain reaction
pre-miRNA Precursor microRNA
qRT-PCR Quantitative reverse transcriptase polymerase chain reaction
RNA Ribonucleic acid
siRNA Small interfering RNA
snRNA Small nuclear RNA
SVM Support vector machines

TERMS

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment. For example, a patient diagnosed with HCC may undergo liver resection as a primary treatment and antisense miR-221 and miR-222 therapy as an adjunctive therapy.

Candidate: As used herein, a "candidate" for therapy is a patient that has TRAIL-Resistant TRAIL Expression Pattern.

Clinical outcome: Refers to the health status of a patient following treatment for a disease or disorder, such as HCC, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Control: A "control" refers to a sample or standard used for comparison with an experimental sample, such as a tumor sample obtained from a patient having TRAIL-resistant cancer. In some embodiments, the control is a liver sample obtained from a healthy patient or a non-cancerous tissue sample obtained from a patient diagnosed with HCC. In some embodiments, the control is a historical control or standard value (i.e. a previously tested control sample or group of samples that represent baseline or normal values, such as the level Trail Expression Pattern in non-cancerous tissue).

Cytokines: Proteins produced by a wide variety of hematopoietic and non-hematopoietic cells that affect the behavior of other cells. Cytokines are important for both the innate and adaptive immune responses.

Decrease in survival: As used herein, "decrease in survival" refers to a decrease in the length of time before death of a patient, or an increase in the risk of death for the patient.

Detecting level of expression: For example, "detecting the level of miR-221 and miR-222 expression" refers to quantifying the amount of miR-221 and miR-222 present in a sample. Detecting expression of miR-221 and miR-222, or any microRNA, can be achieved using any method known in the art or described herein, such as by qRT-PCR. Detecting expression of miR-221 and miR-222 includes detecting expression of either a mature form of miR-221 and miR-222 or a precursor form that is correlated with miR-221 and miR-222 expression. Typically, miRNA detection methods involve sequence specific detection, such as by RT-PCR. miR-221 and miR-222-specific primers and probes can be designed using the precursor and mature miR-221 and miR-222 nucleic acid sequences, which are known in the art and include modifications which do not change the function of the sequences.

Hepatocellular carcinoma (HCC): HCC is a primary malignancy of the liver typically occurring in patients with inflammatory livers resulting from viral hepatitis, liver toxins or hepatic cirrhosis (often caused by alcoholism).

MicroRNA (miRNA, miR): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

miR-221 and miR-222 expression: As used herein, "low miR-221 and miR-222 expression" and "high miR-miR-221 and miR-222 expression" are relative terms that refer to the level of miR-221 and miR-222 found in a sample, such as a healthy or HCC liver sample. In some embodiments, low and high miR-221 and miR-222 expression are determined by comparison of miR-221 and miR-222 levels in a group of non-cancerous and HCC liver samples. Low and high expression can then be assigned to each sample based on whether the expression of miR-221 and miR-222 in a sample is above (high) or below (low) the average or median miR-221 and miR-222 expression level. For individual samples, high or low miR-221 and miR-222 expression can be determined by comparison of the sample to a control or reference sample known to have high or low expression, or by comparison to a standard value. Low and high miR-221 and miR-222 expression can include expression of either the precursor or mature forms or miR-221 and miR-222, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as HCC) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect TRAIL Expression Patterns. In some cases, screening involves contacting a candidate agent (such as an antibody, small molecule or cytokine) with TRAIL-resistant cancer cells and testing the effect of the agent on TRAIL Expression Patterns. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. For example, therapeutic agents for TRAIL-resistant cancer cells include agents that prevent or inhibit development or metastasis of TRAIL-resistant cancer cells. As used herein, a "candidate agent" is a compound selected for screening to determine if it can function as a therapeutic agent for TRAIL-resistant cancer cells. In some embodiments, the candidate agent is identified as a therapeutic agent if the agent converts the cell from in TRAIL-resistant cancer cells. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically effective amount: A quantity of a specified pharmaceutical or therapeutic agent sufficient to achieve a desired effect in a subject, or in a cell, being treated with the agent. For example, this can be the amount of a therapeutic agent that decreases expression of miR-221 and miR-222 and c-Jun or decreases the expression of miR-221 and miR-222 in conjunction with increasing PTEN and/or TIMP3 thereby prevents, treats or ameliorates TRAIL-resistant cancer cells in a patient. The effective amount of the agent will be dependent on several factors, including, but not limited to the subject or cells being treated, and the manner of administration of the therapeutic composition.

TRAIL Expression Pattern: the comparative expression levels of four genes in a cell, cell culture, or tissue sample, including c-Jun, miR-221 and miR-222, PTEN and TIMP3.

TRAIL-resistant TRAIL Expression Pattern: is a TRAIL expression pattern wherein c-Jun and miR-221 and miR-222 expression is high, and PTEN and TIMP3 expression is low compared to control.

TRAIL resistant cancer cells, TRAIL resistant cancer, TRAIL resistant tumor cells or tumor, and the like: cells (in vitro, in situ, in vivo) which, if challenged with TRAIL, no or little apoptosis in response to TRAIL would be observed compared to control. This definition does not require TRAIL challenge testing of every putative TRAIL resistant cell in order to meet the definition; rather, sampling, staining, phenotypic or genetic marker identification, known TRAIL status, or any other suggestion of TRAIL resistance, is within the meaning of this definition.

TRAIL-sensitive TRAIL Expression Pattern: is a TRAIL expression pattern wherein c-Jun and miR-221 and miR-222 expression is low, and PTEN and TIMP3 expression is high compared to control.

Tumor, neoplasia, malignancy or cancer: The result of abnormal and uncontrolled growth of cells. Neoplasia, malignancy, cancer and tumor are often used interchangeably and refer to abnormal growth of a tissue or cells that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Tumor-Node-Metastasis (TNM): The TNM classification of malignant tumors is a cancer staging system for describing the extent of cancer in a patient's body. T describes the size of the primary tumor and whether it has invaded nearby tissue; N describes any lymph nodes that are involved; and M describes metastasis. TNM is developed and maintained by the International Union Against Cancer to achieve consensus on one globally recognized standard for classifying the extent of spread of cancer. The TNM classification is also used by the American Joint Committee on Cancer and the International Federation of Gynecology and Obstetrics.

In some embodiments, the control is non-cancerous tissue sample obtained from the same patient. In other embodiments, the control is a liver sample obtained from a healthy subject, such as a healthy liver donor. In another example, the control is a standard calculated from historical values. Tumor samples and non-cancerous tissue samples can be obtained according to any method known in the art. For example, tumor and non-cancerous samples can be obtained from HCC patients that have undergone liver resection, or they can be obtained by extraction using a hypodermic needle, by microdissection, or by laser capture. Control (non-cancerous) samples can be obtained, for example, from a cadaveric donor or from a healthy liver donor.

In some embodiments, screening comprises contacting the candidate agents with cells. The cells can be primary cells obtained from a patient, or the cells can be immortalized or transformed cells.

The candidate agents can be any type of agent, such as a protein, peptide, small molecule, antibody or nucleic acid. In some embodiments, the candidate agent is a cytokine. In some embodiments, the candidate agent is a small molecule. Screening includes both high-throughput screening and screening individual or small groups of candidate agents.

Methods of Detecting RNA Expression

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32: D109-D111, 2004).

Detection and quantification of RNA expression can be achieved by any one of a number of methods well known in the art (see, for example, U.S. Patent Application Publication Nos. 2006/0211000 and 2007/0299030, herein incorporated by reference) and described below. Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and UI small nuclear RNA (snRNA)). In addition, extraction procedures such as those using TRIZOL™ or TRIREAGENT™, will purify all RNAs, large and small, and are efficient methods for isolating total RNA from biological samples that contain miRNAs and small interfering RNAs (siRNAs).

Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005, each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and HCC liver tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long Oligonucleotide Arrays are composed of 50 to 70-mer oligonucleotide capture probes, and are produced by either ink jet or robotic printing. Short Oligonucleotide Arrays are composed of 20-25-mer oligonucleotide probes, and are produced by photolithographic synthesis (Affymetrix) or by robotic printing.

Quantitative RT-PCR

Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined. However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined.

The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In Situ Hybridization

In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or HCC liver sample. Since the sequences of miR-26 family members are known, miR-26 probes can be designed accordingly such that the probes specifically bind miR-26.

In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Use of miR-221 and miR-222 and c-Jun, PTEN and TIMP3 as predictive markers of prognosis and for identification of therapeutic agents for treatment of TRAIL resistant cancer cells It is disclosed herein that expression patterns of miR-221 and miR-222, c-Jun, PTEN and TIMP3 are predictors of survival prognosis in TRAIL-resistant patients. TRAIL resistant cancer cells samples (for example, tissue biopsy samples) with high miR-221 and miR-222 and c-Jun expression, along with low PTEN and TIMP3 expression compared to non-cancerous tissue from the same subject or from a healthy subject, predicts a decrease in survival. Thus, the TRAIL Resistant Expression Pattern status in tumors can be used as a clinical tool in TRAIL-resistant cancer patients' prognosis.

In some embodiments, the expression level of the markers herein in a TRAIL-resistant tumor sample is directly compared with the TRAIL Resistant Expression Pattern in surrounding non-cancerous tissue from the same patient.

In other embodiments, TRAIL Resistant Expression Pattern in the tumor sample is compared to the TRAIL Resistant Expression Pattern in a liver sample obtained from a healthy subject, such as a liver donor. In some cases, the non-cancerous tissue used as a control sample is obtained from a cadaver. In other embodiments, the TRAIL Resistant Expression Pattern in the tumor sample is compared with a standard level based on historical values. For example, the standard can be set based on average Trail Resistant Expression Pattern in non-cancerous liver tissue samples obtained from a cohort of subjects. For instance, the cohort of subjects can be a group of HCC patients enrolled in a clinical trial. The cohort of subject can also be a group of cadaveric donors.

Finding a TRAIL Resistant Expression Pattern in a HCC tumor sample relative to a control indicates a poor prognosis for the patient and identifies the patient as a good candidate for specialized therapy. As used herein, "poor prognosis" generally refers to a decrease in survival, or in other words, an increase in risk of death or a decrease in the time until death. Poor prognosis can also refer to an increase in severity of the disease, such as an increase in spread (metastasis) of the cancer to other organs. In one embodiment, TRAIL Resistant Expression Pattern is found when the respective markers show at least a 1.5-fold increase or decrease in expression relative to the control. In other embodiments, TRAIL Resistant Expression Pattern is indicated by at least a 2-fold, at least a 2.5-fold, at least a 3-fold, at least a 3.5-fold, or at least a 4-fold increase or decrease in the markers of TRAIL Resistant Expression Pattern relative to the control.

The finding that patients with TRAIL resistant tumors having a TRAIL sensitive Expression Pattern have a better chance of survival indicates that compounds that decrease c-Jun, miR-221 and miR-222 expression in conjunction with increasing PTEN and TIMP3 expression will be useful as therapeutic agents for the treatment of TRAIL resistant tumors.

Thus, provided herein is a method of identifying therapeutic agents for the treatment of TRAIL resistant cancer cells, comprising screening candidate agents in vitro to select an agent that promote conversion from TRAIL Resistant TRAIL Expression Pattern to TRAIL Sensitive TRAIL Expression Pattern. In some embodiments, screening comprises contacting the candidate agents with TRAIL resistant cancer cells and detecting any change TRAIL Expression Pattern. The TRAIL resistant cancer cells can be primary cells obtained from a patient, immortalized or transformed cells obtained from a patient, or the cells can be commercially available immortalized cell lines, such as, but not limited to MHCC97, HepG2, Hep3B or SNU-423 cells.

A conversion to TRAIL sensitive Expression Pattern following treatment with the candidate agent identifies the agent as a therapeutic agent for the treatment of TRAIL resistant cancer. Methods of screening candidate agents to identify therapeutic agents for the treatment of disease are well known in the art. Methods of detecting expression levels of RNA and proteins are known in the art and are described herein, such as, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter TRAIL Expression Pattern(s) either directly or indirectly. In some embodiments, the candidate agents are molecules that play a role in the NFκB/IL-6 signaling pathway. In other embodiments, the candidate agents are molecules that play a role in the IL-10, STAT3 or interferon-inducible factor signaling networks. In one embodiment, the candidate agents are cytokines. In another embodiment, the candidate agents are small molecules.

Also described herein is a method for the characterization of TRAIL resistant cancer, wherein at least one feature of TRAIL resistant cancer is selected from one or more of the group consisting of: presence or absence of TRAIL resistant cancer; diagnosis of TRAIL resistant cancer; prognosis of TRAIL resistant cancer; therapy outcome prediction; therapy outcome monitoring; suitability of TRAIL resistant cancer to treatment, such as suitability of TRAIL resistant cancer to chemotherapy treatment and/or radiotherapy treatment; suitability of TRAIL resistant cancer to hormone treatment; suitability of TRAIL resistant cancer for removal by invasive surgery; suitability of TRAIL resistant cancer to combined adjuvant therapy.

Also described herein is a kit for the detection of TRAIL resistant cancer, the kit comprising at least one detection probe comprising c-Jun and miR-221 and miR-222 or miR-221 and miR-222 and PTEN and/or TIMP3. The kit can be in the form or comprises an oligonucleotide array.

Also described herein is a method for the determination of suitability of a TRAIL resistant cancer patient for treatment comprising: i) isolating at least one tissue sample from a patient suffering from TRAIL resistant cancer; ii) performing the characterization of at least one tissue sample and/or utilizing a detection probe, to identify the TRAIL Expression Pattern; iii) based on the at least one feature identified in step ii), diagnosing the physiological status of the patient; iv) based on the diagnosis obtained in step iii), determining whether the patient would benefit from treatment of the TRAIL resistant cancer.

In certain embodiments, the at least one feature of the cancer is selected from one or more of the group consisting of: presence or absence of the cancer; type of the cancer; origin of the cancer; diagnosis of cancer; prognosis of the cancer; therapy outcome prediction; therapy outcome monitoring; suitability of the cancer to treatment, such as suitability of the cancer to chemotherapy treatment and/or radiotherapy treatment; suitability of the cancer to hormone treatment; suitability of the cancer for removal by invasive surgery; suitability of the cancer to combined adjuvant therapy.

Also described herein is a method of for the determination of suitability of a cancer for treatment, wherein the at least one feature of the cancer is suitability of the cancer to treatment, such as suitability of the cancer to chemotherapy treatment and/or radiotherapy treatment; suitability of the cancer to hormone treatment; suitability of the cancer for removal by invasive surgery; suitability of the cancer to combined adjuvant therapy.

Also described herein is a method for the determination of the likely prognosis of a cancer patient comprising: i) isolating at least one tissue sample from a patient suffering from cancer; and, ii) characterizing at least one tissue sample to identify the TRAIL Expression Pattern; wherein the feature allows for the determination of the likely prognosis of the cancer patient.

The following examples are provided to illustrate certain particular features and/or embodiments. These examples should not be construed to limit the disclosure to the particular features or embodiments described.

EXAMPLES

Example I miR-221 and miR-222 Directly Target PTEN and TIMP3 3'UTRs

Figure 1A:
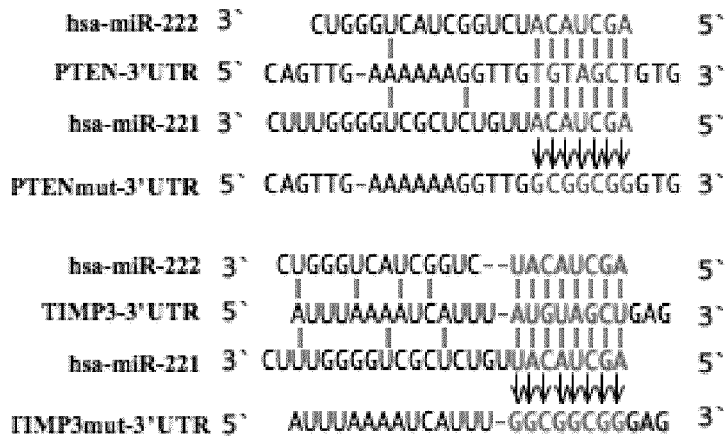
FIGS. 1A-1H. PTEN and TIMP3 are targets of miR-221 and miR-222.
Figure 1B:
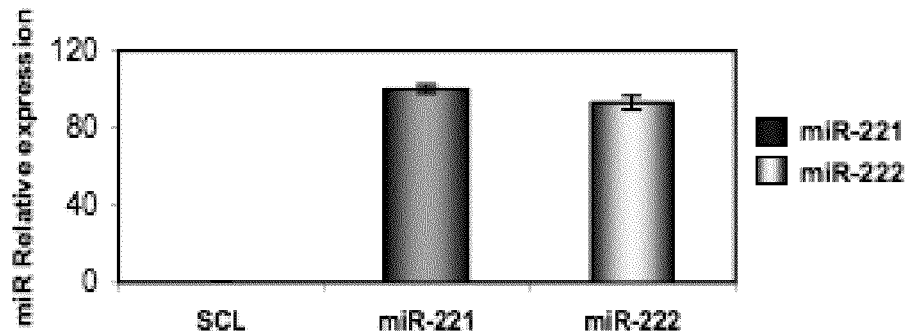
Figure 1C:
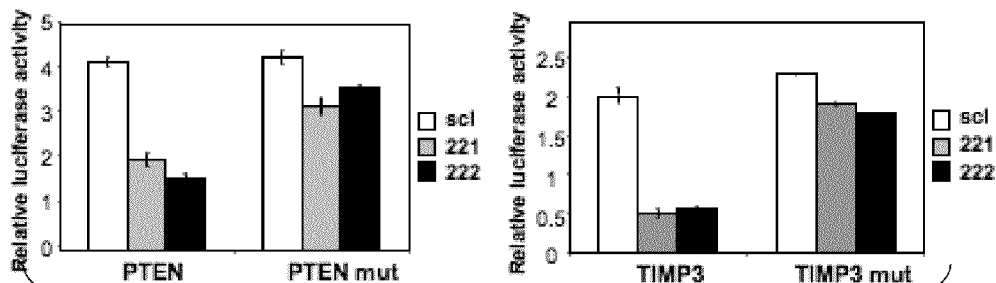
Figure 1D:
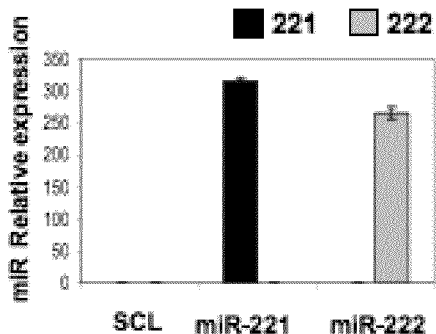
Figure 1E:
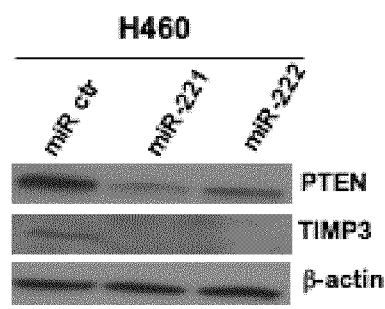
Figure 1F:
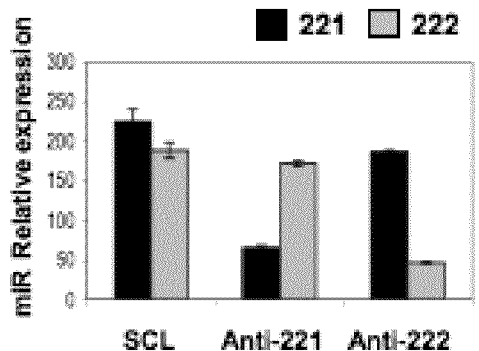
Figure 1G:
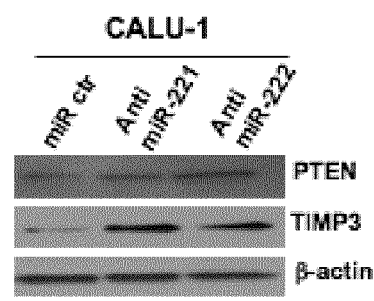

To identify putative miR-221 and miR-222 targets, a bioinformatics search (Targetscan, Pictar, RNhybrid) was conducted. Among the candidate targets, 3'-UTRs of human PTEN (nucleotides 200-207, NM_000314) and human TIMP3 (nucleotides 2443-2449, NM_000362) contained regions that matched the seed sequences of hsa-miR-221 and miR-222 (FIG. 1A). To ascertain whether PTEN and TIMP3 are direct targets of miR-221 and miR-222, PTEN and TIMP3 3' UTR containing the miR-221/miR-222 binding sites were cloned downstream of the luciferase open reading frame. These reporter constructs were used to transfect MEG01 cells, which express very low levels of miR-221 and miR-222 (FIG. 1B) and are highly transfectable (Freson et al., 2005). Increased expression of these miRs upon transfection, confirmed by qRT-PCR (FIG. 1B), significantly affected luciferase expression, measured as relative luciferase activity (FIG. 1C). Conversely, when luciferase assays were performed by using a plasmid harboring the 3' UTR of PTEN and TIMP3 mRNAs, where the binding sites for miR-221 and miR-222 were inactivated by site-directed mutagenesis, there was observed a consistent reduction in miR-221 and miR-222 inhibitory effect (FIG. 1C). To determine if these microRNAs affect PTEN and TIMP3 expression in the H460 cellular environment, the consequences of the ectopic expression of miR-221 and miR-222 in H460 cells were analyzed. Increased expression of these miRs upon transfection was confirmed by qRT-PCR (FIG. 1D) and then the effects on endogenous levels of PTEN and TIMP3 were analyzed by Western blot (FIG. 1E); miR-221 and miR-222 over-expression significantly reduced the endogenous levels of PTEN and TIMP3, compared to H460 cells transfected with scrambled pre-miR. Conversely, knockdown of miR-221 and miR-222 by 2'-O-me-anti-miR-221 and 2'-O-me-anti-miR-222, confirmed by qRT-PCR (FIG. 1F) in Calu-1-lung derived cells with high levels of endogenous miR-221 and miR-222, increased the protein levels of PTEN and TIMP3 (FIG. 1G). Intriguingly, by quantitative RT-PCR, it was found that PTEN, but not TIMP3 mRNA levels, were strongly reduced in the miR-221 and miR-222 transfected cells (FIG. 1H), indicating that miR-221 and miR-222 induce the degradation of PTEN mRNA while TIMP3 is regulated by these microRNAs only at the translational level. PTEN and TIMP3 3' UTRs are therefore direct targets of miR-221 and miR-222.

Figure 1H:
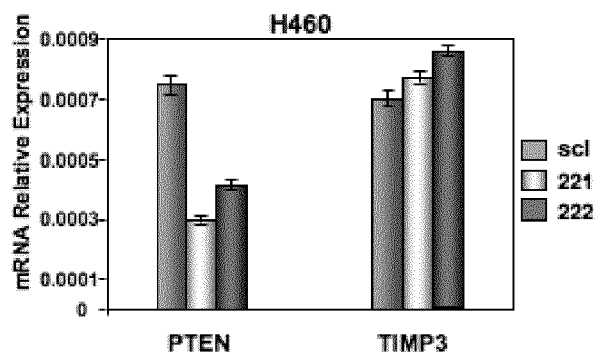
Figure 2A:
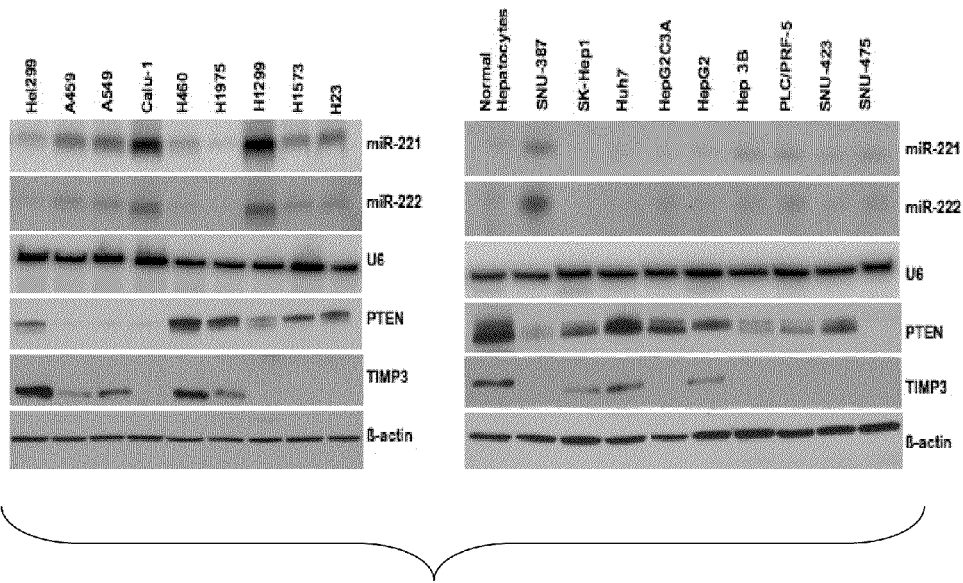
FIGS. 2A-2B. PTEN and TIMP3 expression is inversely related to that of miR-221 and miR-222 in NSCLC and HCC.
Figure 2B:
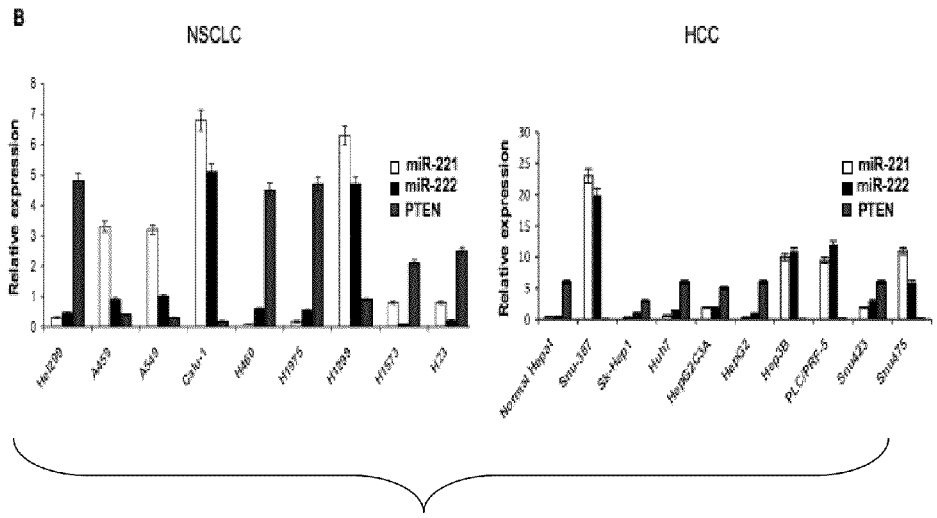

Example II miR-221 and miR-222 are Inversely Correlated with PTEN and TIMP3 Expression in NSCLC and HCC The endogenous levels of miR-221 and miR-222 were evaluated by Northern blot in large panels of primary NSCLCs and HCCs, compared with the normal counterpart. miR-221 and miR-222 expression was almost undetectable in normal lung and liver cells but highly expressed in the majority of tumor cell lines. Moreover, as assessed by Western blot, an inverse correlation between miR-221 and miR-222 RNA expression and PTEN and TIMP3 protein expression was found in most cell lines analyzed (FIG. 2A), confirmed also by qRT-PCR (FIG. 2B). TIMP3 mRNA expression levels was not tested because down-regulation of TIMP3 mRNA after enforced miR-221 and miR-222 expression was not observed (FIG. 1H). These results indicate that high expression of miR-221 and miR-222 is one of the mechanisms acting to negatively regulate PTEN and TIMP3 in NSCLC and HCC.

Figure 3A:
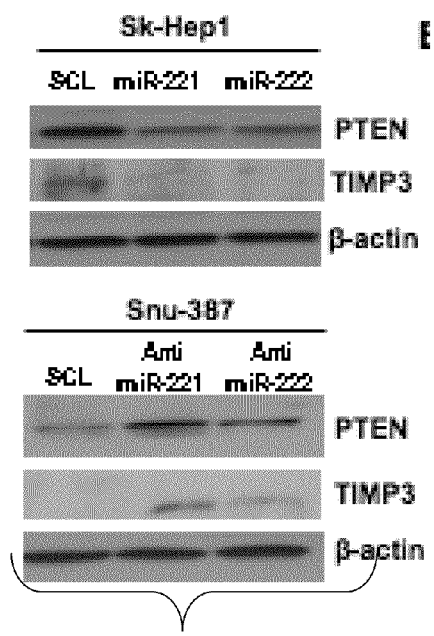
FIGS. 3A-3C. PTEN and TIMP3 are direct targets of miR-221 and miR-222 in HCC in vitro and in vivo.

To verify whether these microRNAs affected PTEN and TIMP3 endogenous levels also in HCC, analysis of the effects of the ectopic expression of miR-221 and miR-222 in the Sk-Hep1 cell line, which expresses low levels of miR-221 and miR-222, was performed. As shown in FIG. 3A, PTEN and TIMP3 proteins were reduced in Sk-Hep1 cells upon miR-221 and miR-222 over-expression. Conversely, knockdown of miR-221 and miR-222 by 2'-O-me-anti-miR-221 and 2'-O-me-anti-miR-222 in Snu-387 cells, which expressed high levels of endogenous miR-221 and miR-222, increased the protein level of PTEN and TIMP3 (FIG. 3A).

Figure 3B:
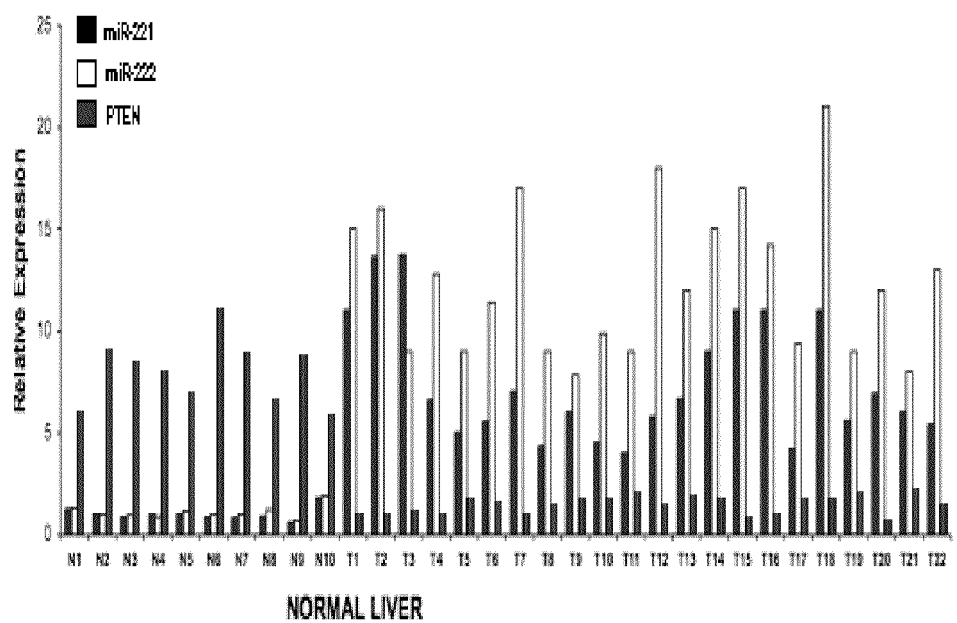

Having noted that miR-221 and miR-222 down-regulate PTEN and TIMP3 expression in both NSCLC and HCC-derived cells in culture, regulation in vivo was studied. To answer this question, PTEN mRNA and miR-221 and miR-222 expression by qRT-PCR in primary lung tumor specimens was studied, in comparison with normal human lung tissue samples. miR-221 and miR-222 were almost undetectable in normal human lung samples and highly expressed in all the tumor samples analyzed. Of the 22 primary lung tumors examined, in fact, all exhibited down-regulation of PTEN and over-expression of miR-221 and miR-222 (FIG. 3B). These data further support the finding that PTEN is a direct target of miR-221 and miR-222 also in vivo.

Figure 3C:
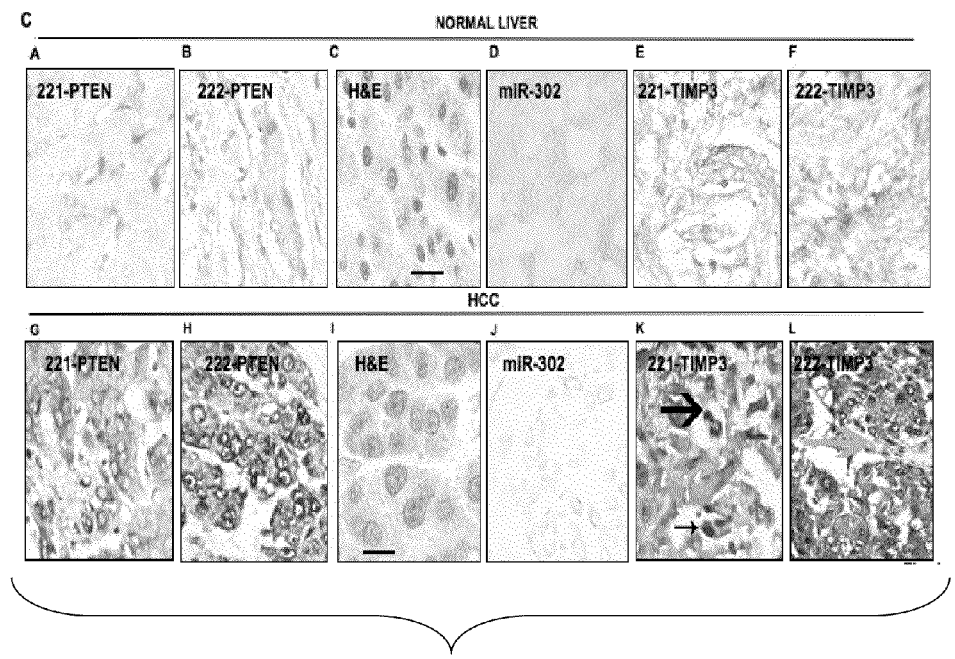
Figures 9A, 9B, 9C, 9D, 9E, 9F, 9G, 9H, 9I, 9J:
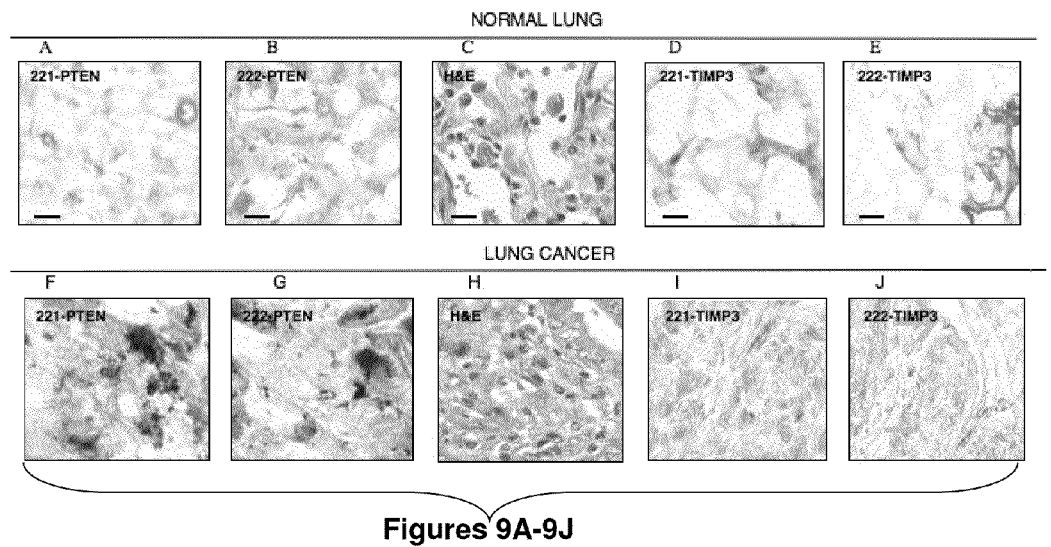
FIGS. 9A-9L. IHC and ISH of miR-221/miR-222 and PTEN/TIMP3 in lung cancers and the adjacent benign tissues. miR-221/miR-222 (blue) and PTEN/TIMP3 (red) expression were inversely related in lung cancers and the adjacent normal lung tissues. These tissues were analyzed for miR-221 and miR-222 expression by in situ hybridization, followed by immunohistochemistry for PTEN and TIMP3 as described in the "Supplemental Experimental Procedures". The majority of cancer cells were positive for miR-221 and miR-222 and negative for PTEN (FIGS. 9F-9G) and TIMP3 (FIGS. 9I-9J). Conversely, the normal cells were negative for miR-221/miR-222 (FIGS. 9A-9B-9D-9E) and positive for PTEN and TIMP3. Note that in several cancers (FIGS. 9I and 9J) miR-221/miR-222 expression was evident with TIMP3 expression; however the miRNA expression was evident in the cancer cells and the TIMP3 expression in the surrounding cells in the desmoplastic tissue.
Figure 9K:
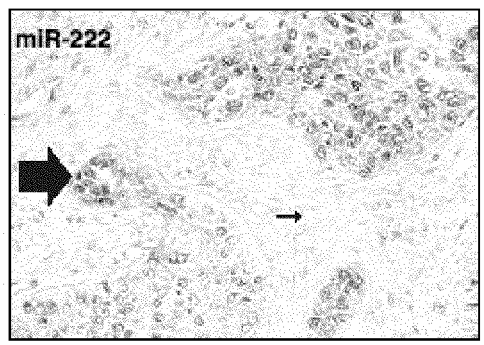
Figure 9L:
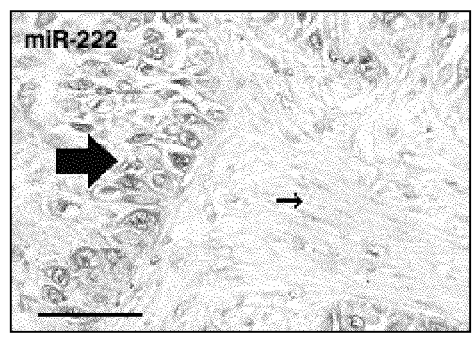

To corroborate these findings, in situ hybridization analysis was performed, by using 5'-dig-labeled LNA probes, on hepatocarcinoma and normal liver tissues, followed by immunohistochemistry for PTEN and TIMP3 (FIG. 3C). miR-221/miR-222 and PTEN/TIMP3 expressions were inversely related in liver cancers and the adjacent normal/cirrhotic liver tissues. Liver cancer cells showed high expression of miR-221/miR-222 and rarely expressed PTEN or TIMP3 (FIG. 3CG-H-K-L) whereas the adjacent non-malignant liver expressed PTEN and TIMP3 abundantly and rarely showed detectable miR-221/miR-222 signal (FIG. 3CA-B-E-F). miR-221/miR-222 and PTEN/TIMP3 expression were also inversely related in lung cancers and the adjacent normal lung tissues (FIG. 9). The majority of cancer cells were positive for miR-221 and miR-222 and negative for PTEN (FIGS. 9F-9G) and TIMP3 (FIGS. 9I-9J). In FIGS. 9I-9J miRNA expression was evident in the cancer cells and TIMP3 expression in the surrounding cells. A strong miR-222 signal (large arrow) was found in the nests of tumor cells that are infiltrating the adjacent fibrotic lung tissue (FIGS. 9K-9L).

Example III miR-221 and miR-222 Induce TRAIL Resistance in NSCLC and HCC by Targeting PTEN and TIMP3

Figure 4A:
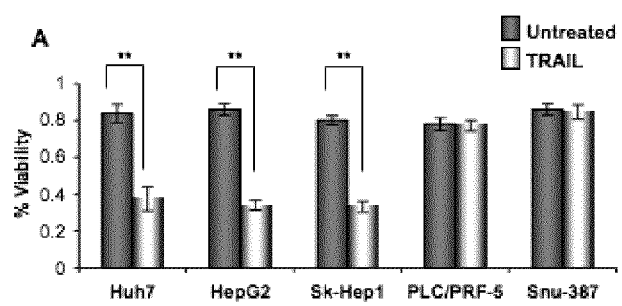
FIGS. 4A-4E. miR-221 and miR-222 induce TRAIL-resistance in NSCLC and HCC by targeting PTEN and TIMP3.

The effects of miR-221 and miR-222 and/or PTEN-TIMP3 silencing on cell survival and TRAIL resistance in both NSCLC and HCC were studied. First there was performed a proliferation assay on 5 HCC-derived cell lines, three of them (HepG2, Sk-Hep1 and Huh 7) with low miR-221-miR-222 expression and two (PLC/PRF-5 and Snu-387) with high miR-221-miR-222 expression level (FIG. 4A). Cells were exposed to TRAIL for 24 hours and subsequently cell proliferation was assessed using an MTT assay. Interestingly, cells expressing low levels of miR-221 and miR-222 underwent TRAIL-induced cell death, showing a very low proliferation rate, whereas cells over-expressing miR-221 and miR-222 did not display sensitivity when exposed to soluble TRAIL (FIG. 4A).

Figure 4B:
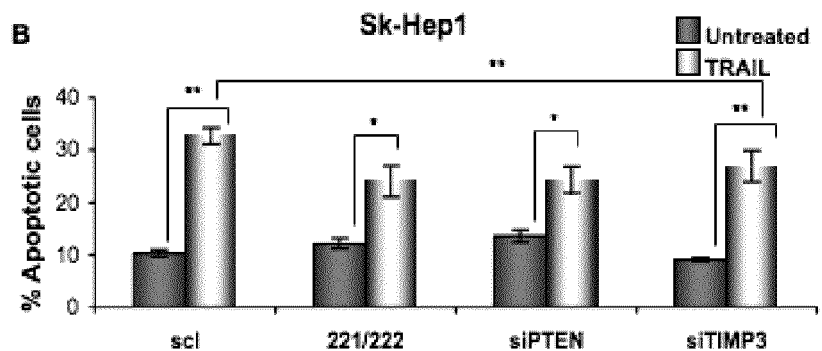
Figure 4C:
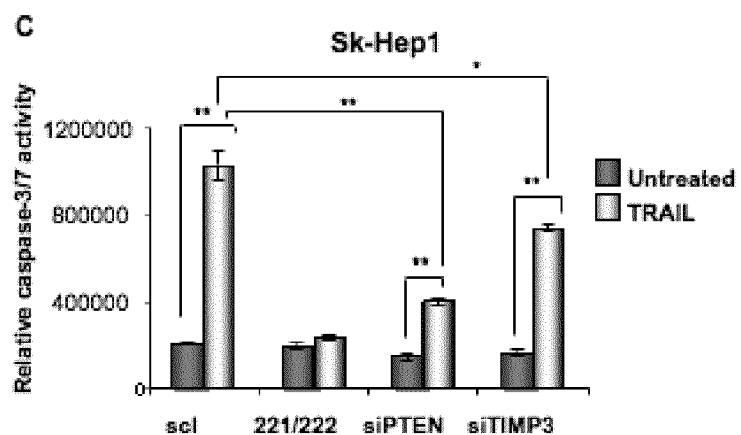
Figure 4D:
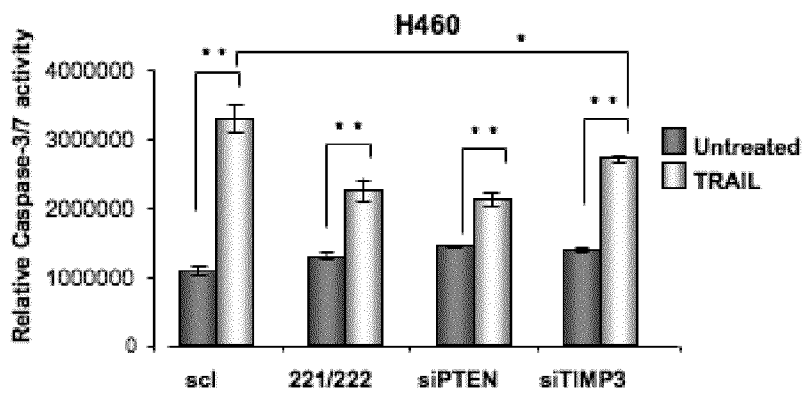
Figure 4E:
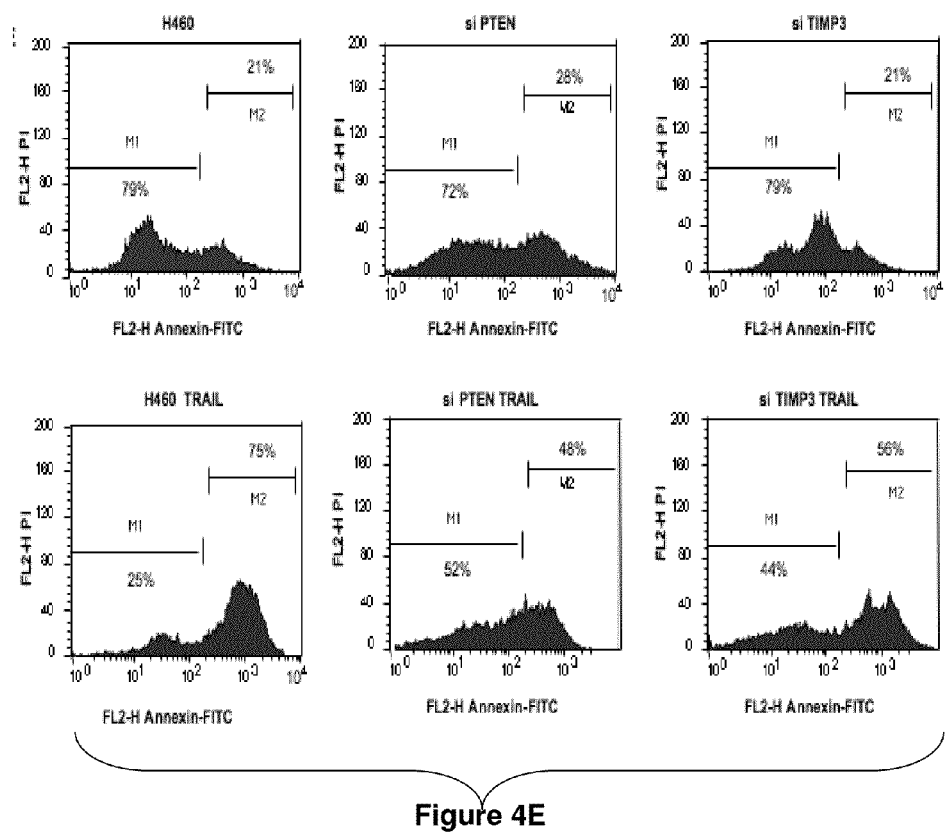
Figure 10A:
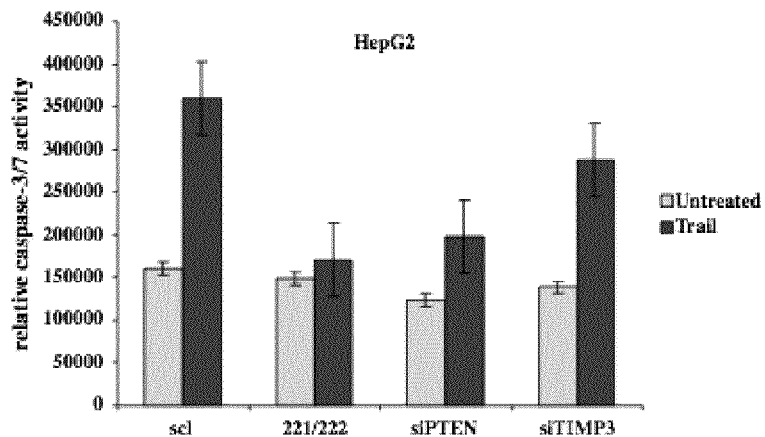
FIGS. 10A-10B. Caspase 3/7 activity in HepG2 and Huh7 cells after miR-221 and miR-222 upregulation or PTEN/TIMP3 knockdown. For caspase 3/7 activity detection, cells were cultured in 96-well plates, transfected with 100 nM miR-221 and miR-222 for 72 h. After 48 h from transfection cells were treated with TRAIL 400 ng/ml for 24 h and analyzed using Caspase-Glo 3/7 Assay kit according to the manufacturer's instructions. HepG2 and Huh7 cells became resistant to TRAIL inducing apoptosis after miR-221 and miR-222 forced expression or PTEN/TIMP3 downregulation. Data are presented as ±SD.
Figure 10B:
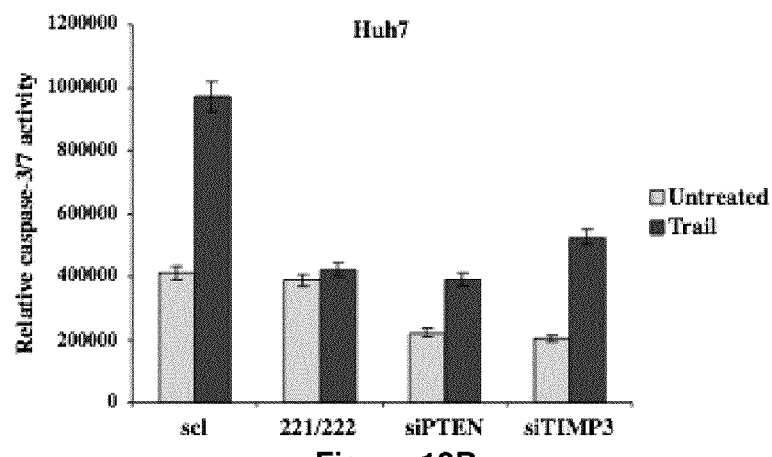

Moreover, Annexin-FITC and caspase 3/7 assays on TRAIL-sensitive cell lines Sk-Hep1 cells, (FIGS. 4B-4C), HepG2 and Huh7 (FIGS. 10A-10B), revealed an increase of about 30-40% in TRAIL resistance after miR-221 and miR-222 over-expression, as well as after PTEN and TIMP3 silencing by PTEN and TIMP3 siRNAs. TRAIL-sensitive H460 cells also became more resistant to TRAIL inducing-apoptosis after PTEN and TIMP3 knockdown, as determined by caspase 3/7 activity (FIG. 4D) and Annexin-FITC assay (FIG. 4E), although PTEN silencing was more effective than TIMP3.

Moreover, to further evaluate the contribution of these targets on TRAIL-inducing apoptosis, PTEN and TIMP3 sequences were cloned in pCruz-HA plasmid (Santa Cruz) and used to transfect Calu-1 TRAIL-resistant cells. Calu-1 cells became more sensitive to TRAIL inducing-apoptosis after PTEN and TIMP3 restoration, alone or in combination, as determined by caspase 3/7 activity (FIG. 4D) and Annexin-FITC staining (FIG. 11A-11B). To further investigate the role of TIMP3 in TRAIL-inducing apoptosis the expression of caspase-3,-8-9, poly-ADP-ribose polymerase (PARP) and some of the molecule involved in the TRAIL-signaling pathway were tested by western blot after TIMP3 overexpression in Calu-1 cell line (FIG. 11C). Interestingly, the activation of PARP and the caspase cascade were observed, as assessed by the appearance of the cleaved fragments. Moreover, Mc1-1 expression was down-regulated while cytochrome c expression increased (FIG. 11C).

All together these results suggest an involvement of TIMP3 in both the extrinsic and intrinsic apoptotic pathways and highlight its role in TRAIL-inducing apoptosis. The same results were obtained after TIMP3 restoration in Snu-387 cells (data not shown).

Figures 5A, 5B:
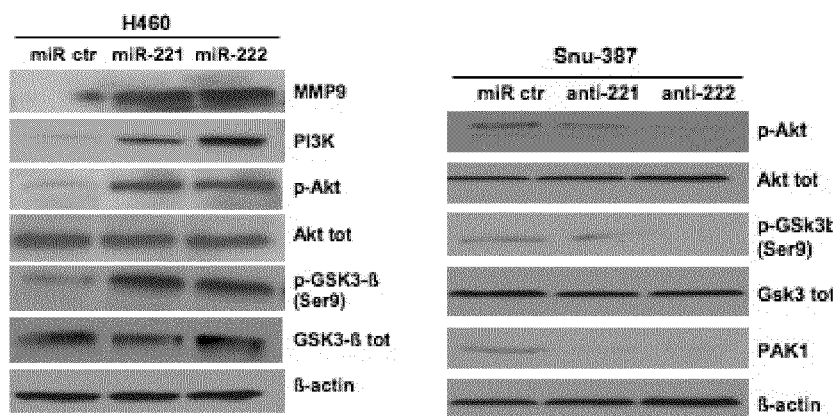

Further, the expression and/or the activation of some of the proteins involved in the PI3K/AKT pathway after miR-221 and miR-222 enforced expression in H460 cells or after miR-221/miR-222 silencing in Snu-387 cells was conducted. As shown in FIG. 5A, the expression levels of PI3K, AKT and its phosphorylated substrate, phospho-glycogen synthase kinase 3, were elevated by ectopic expression of miR-221 and miR-222, and, in contrast, were decreased by knockdown of miR-221 and miR-222 in Snu-387 cells, indicating that miR-221 and miR-222 target the PTEN/AKT pathway (FIG. 5B).

Further investigation of the activation and expression levels of these proteins was conducted. There was found an increase in ERKs phosphorylation and PAK1 expression, as compared with H460 cells transfected with the control miR (FIG. 5C). Interestingly, increased expression of metallopeptidase 3 and metallopeptidase 9 was also found, as possible result of TIMP3 down-regulation (FIGS. 5A-5C). To test if the activation of the previous proteins was PTEN and/or TIMP3-dependent, PTEN and TIMP3 were silenced in H460 cells. As shown in FIGS. 5D and E the activation of the ERKs and PAK1 is both PTEN and TIMP3-dependent, while AKT phosphorylation is PTEN-dependent and MMP3 and MMP9 are upregulated after TIMP3 knockdown.

Figure 5G:
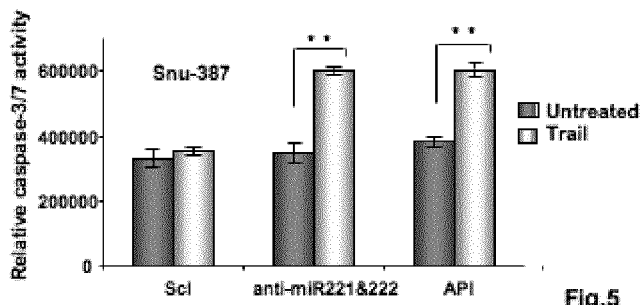

Finally, AKT inhibition was studied, as it relates to whether it could override miR-221 and miR-222-induced cell survival and TRAIL-resistance. Calu-1 and Snu-387 were transfected with 2'-O-methyl (2'-O-me)-anti-miR-221 and miR-222 oligoribonucleotides. Cells transfected with 2'-O-me-scrambled miR were used as control. Blocking miR-221 and miR-222 expression considerably sensitized these cells to TRAIL-induced apoptosis, as assessed by caspase 3/7 assay (FIGS. 5F-5G). Moreover, Calu-1 and Snu-387 cells were treated with the specific AKT inhibitor, API-2/triciribine, with or without TRAIL. As shown in FIGS. 5F and 5G, API-2 abrogated miR 221 and miR-222-activated AKT and significantly inhibited miR-221 and miR-222-induced cell survival and TRAIL resistance.

Next, to directly compare the growth of tumors with and without PTEN and TIMP3, short hairpin RNA (shRNA) constructs, designed to knockdown gene expression, were used to silence PTEN and TIMP3 in H460 cells. An shRNA plasmid, encoding a scrambled shRNA sequence that does not lead to the specific degradation of any known cellular mRNA, was used as control. The consequences of PTEN and TIMP3 disruption on tumor growth and TRAIL resistance was assessed in vivo by implanting H460 PTEN and TIMP3 knockdown cells into the right dorsal sides of nude mice. TRAIL treatment was initiated 5 days afterwards, when lung carcinoma had been established. PTEN and TIMP3 loss (FIG. 12A) conferred not only a significant tumor growth advantage but also resistance to TRAIL-inducing apoptosis over control tumors (FIGS. 124B-12C-12D-2E-12F-12G).

In conclusion, PTEN and TIMP3 are important targets in TRAIL resistance and play an important role in tumorigenicity of NSCLC and HCC cells.

Example IV

Figure 6A:
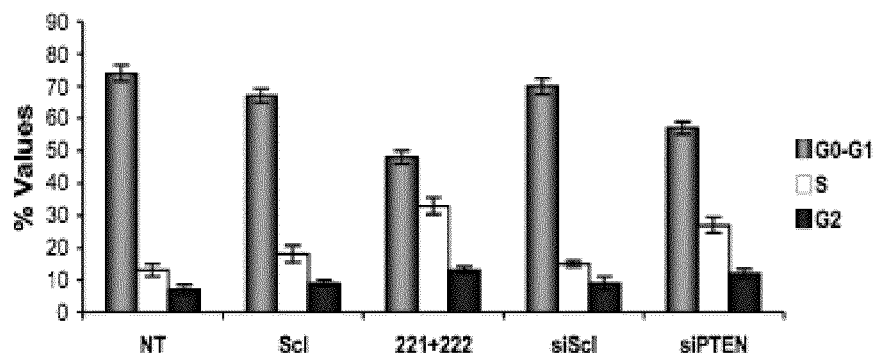
FIGS. 6A-6D. Ectopic expression of miR-221 and miR-222 affects the cell cycle distribution and migration/invasion capabilities of H460 cells.

PTEN and TIMP3 Down-Regulation by miR-221 and miR-222 Induces Migration and Invasiveness in NSCLC and HCC Cells To directly test the functional role of miR-221/miR-222 in tumorigenesis, these two microRNAs were over-expressed, or PTEN and TIMP3 were silenced, in H460 and Sk-Hep1 cells. Then, by cell cycle analysis, miR-221 and miR-222 and PTEN siRNA H460 transfected cells showed a decrease of G1 and a corresponding increase of the S and G2-M phases (FIG. 6A). After 72 h of transfection the analysis revealed an earlier onset of DNA synthesis induced by miR-221 and miR-222 or PTEN knockdown, paralleled by a faster reduction of G1 cells, contributing to the proliferative advantage (FIG. 6A). The same change was observed in Sk-Hep1 cells (FIG. 13A).

Figure 6B:
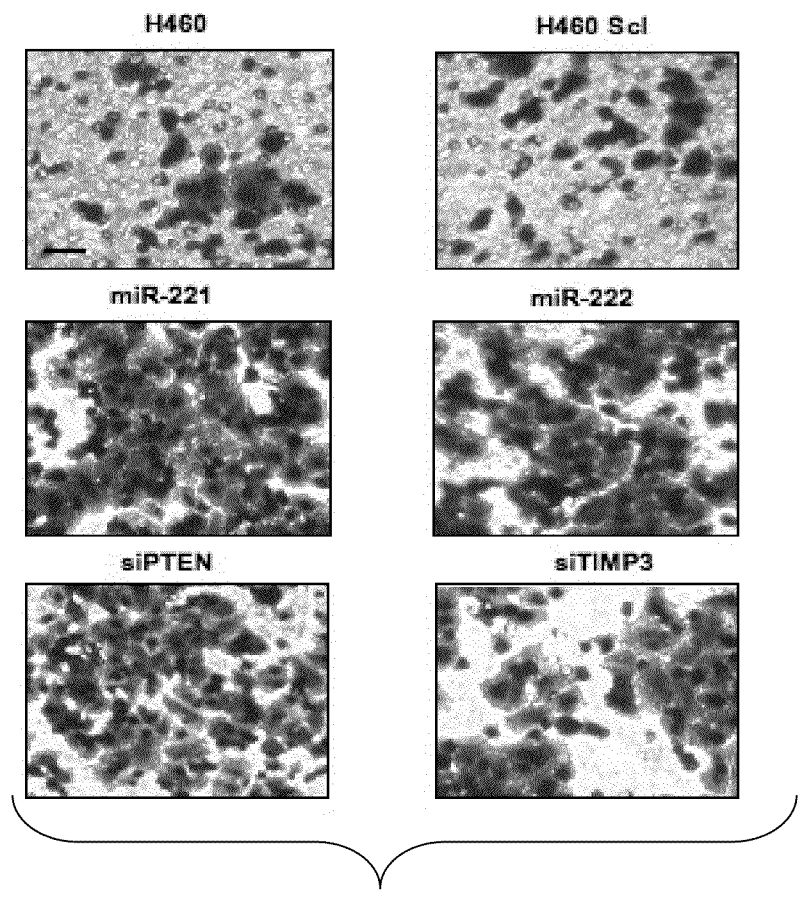
Figure 6C:
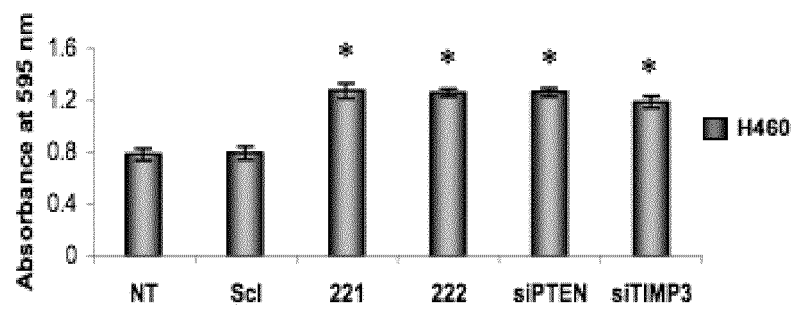
Figure 6D:
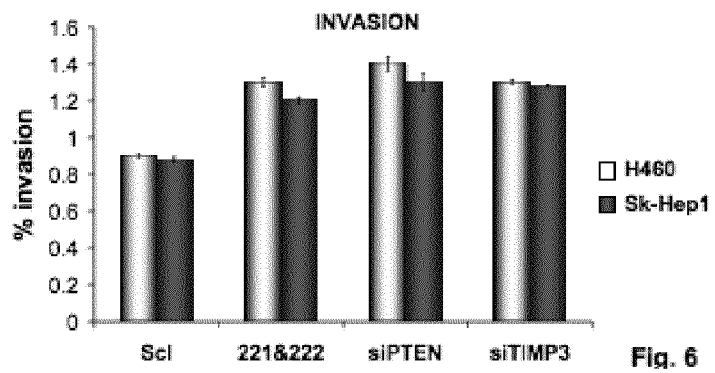

Next, the inventors analyzed the effects of miR-221 and miR-222 over-expression on cellular migration and invasion of NSCLC and HCC cells. Interestingly, a significant increase on the migratory (FIGS. 6B-6C) and invasive (FIG. 6D) capabilities of H460 and Sk-Hep1 (FIG. 113B) cells after miR-221 and miR-222 overexpression as well after PTEN and TIMP3 downregulation was observed. Conversely, when miR-221 and miR-222 were down-regulated by transfection with 2'-O-me-anti-miR-221 and miR-222, a decrease in cell migration and invasion in both Calu-1 and Snu-387 cells (FIGS. 14A-14B) was observed.

Example V

MET Controls miR-221 and miR-222 Activation Through AP-1 Transcription Factor

Figure 7A:
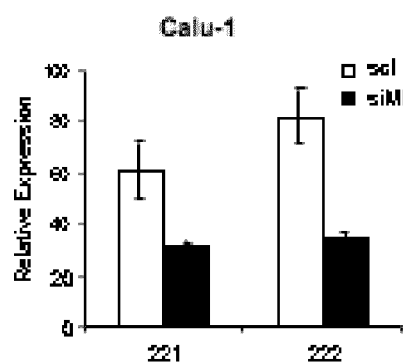
Figure 7B:
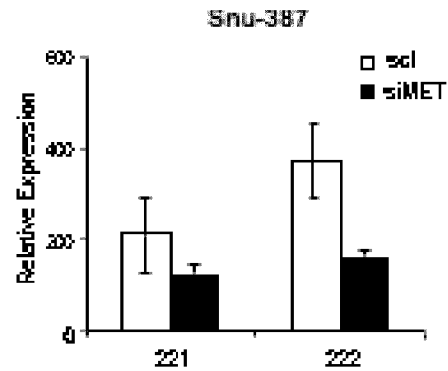
Figure 7C:
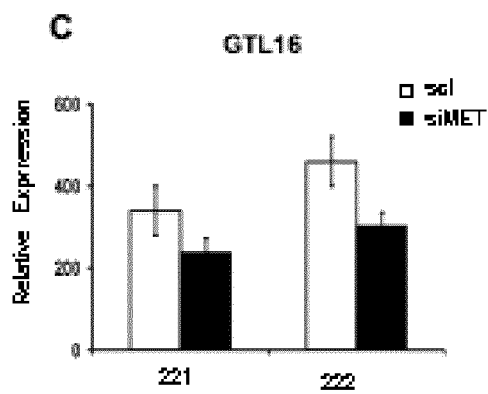

MET was silenced by using siRNA, in Calu-1 and Snu-387 cells and in a gastric cell line (GTL16), previously reported to over-express MET oncogene due to DNA amplification (Giordano et al., 1989). First, miR-221 and miR-222 expression levels were evaluated by qRT-PCR. After MET knockdown, miR-221 and miR-222 expression was down-regulated in all cell lines analyzed (FIGS. 7A-7B-7C). The same result was obtained by treating GTL16 cells with a MET inhibitor, SU11274 (FIG. 15A).

Figure 7D:
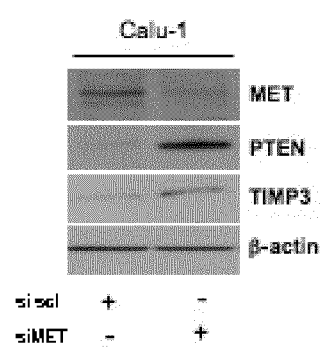

Secondly, by immunostaining, there was observed increased PTEN and TIMP3 expression levels after MET down-regulation or inhibition, indicating that MET is involved in miR-221 and miR-222 activation (FIGS. 7D-7E-7F).

Next, by bioinformatics search (TESS database: http://www.cbil.upenn.edu/cgi-bin/tess/tess), it was found that the only transcription factor involved in the MET pathway predicted to bind and transcriptionally activate miR-221/miR-222 promoter was AP-1. AP-1 is a dimeric basic region-leucine zipper protein that belongs to the Jun and Fos subfamilies c-Jun is the most potent transcriptional activator in its group.

To identify which factor belonging to the AP-1 family was involved in miR-221/miR-222 transcriptional activation, the correlation between miR-221 and miR-222 expression and c-Jun and c-Fos protein levels in 4 different cell lines (H460, Calu-1, Huh7 and Snu-387) (FIG. S7B) was studied. Calu-1, highly expressing c-Jun and c-Fos, were co-transfected with MET siRNA, c-Jun siRNA or c-Fos siRNA. Subsequent qRT-PCR amplification showed that MET and c-Jun down-regulation, but not c-Fos knockdown, gave rise to a reduction of ~45-50% in miR-221 and miR-222 expression levels, as compared with the negative control (FIG. S7C).

To further confirm these results luciferase assays were conducted. In previous work, the inventors found that miR-221 and miR-222 are transcribed into a single species of 2.1 kb RNA and the transcription is regulated by the upstream sequence located at −150 bp/50 bp from the 5' end of miR-222 hairpin structure. To determine if the previously identified miR-221 and miR-222 promoter region was affected by MET/AP1, the luciferase assay was performed by using the reporter plasmids containing the fragments spanning +3~−150, +3~−600, +3~−1000 (+1 position corresponds to the 5' terminus of miR-222 hairpin) (FIG. 7G) into the pGL3basic vector which harbors the promoter-less luciferase gene (Di Leva et al., unpublished data). The pGL3b, −150, −600 and −1000 pGL3b were co-transfected with MET siRNA, c-Jun siRNA or c-Fos siRNA into Calu-1 cells (FIGS. 15D-15E).

Subsequent luciferase assays showed that MET and c-Jun down-regulation gave rise to a reduction of ~45% in luciferase activity, as compared to the basal activity determined by transfection with pGL3b empty vector; the inventors did not observe a reduction of luciferase activity after c-Fos siRNA transfection (FIGS. 15D-15E).

These data indicate that c-Jun and not c-Fos is the transcription factor involved in the MET pathway, responsible for miR-221 and miR-222 activation in NSCLC and HCC cells.

Since the promoter region was responsive to c-Jun modulation, to verify a direct binding of c-Jun on miR-221 and miR-222 promoter, a chromatin immunoprecipitation (ChIP) assays was conducted. First, by bioinformatics analysis, it was found that only one AP-1 putative binding site is located ~130 bp upstream of the premiR-222-5' end. Taking into account the predicted AP-1 binding site, a total of 2 chromatin regions were analyzed (FIG. 7G): one spanning the AP-1 binding site and the second, as negative control, ~1700 nt upstream of the pre-miR-222-5' end, where the inventors did not find any predicted binding site for AP-1. The ChIP assay of c-Jun positive Calu-1 and Snu-387 cells showed remarkable AP-1 binding at ChIP analyzed region 2, proximal to the promoter (FIGS. 7H-7I). No chromatin enrichment by c-Jun ChIP was observed in c-Jun negative H460 cells, verifying the specificity of the ChIP assay.

Finally, Huh7 cells, which show low levels of miR-221 and miR-222, were treated with anisomycin, an antibiotic able to activate JNK kinases, and, thus AP-1, miR-221 and miR-222 and PTEN-TIMP3 expression levels were checked. After c-Jun activation (FIG. 7M) by anisomycin, miR-221 and -222 expression increased (miR-221=80%, miR-222=40%) as confirmed by qRT-PCR (FIG. 7L), while PTEN and TIMP3 expression levels were decreased drastically (FIG. 7 M). To further prove that JNK is the intermediate signaling factor between c-Met and c-Jun and that c-Jun knockdown leads to increased PTEN and TIMP3 expression, c-Met and c-Jun in Calu-1 cells were studied and the JNK1/2 phosphorylation and PTEN and TIMP3 expression were analyzed, respectively. As shown in FIG. S7F, MET knockdown reduces JNK1/2 phosphorylation while c-Jun silencing increases PTEN/TIMP3 expression as result of miR-221 and miR-222 down modulation.

To investigate whether there is a direct relation between MET and PTEN/TIMP3 in vivo, immunohistochemistry analysis was performed on lung and liver cancer and normal samples. The co-labeling MET/PTEN and MET/TIMP3 showed that PTEN and TIMP3 are abundantly expressed only in the normal cells, where MET is not present, whereas c-Met is expressed exclusively in the cancer cells (FIG. 16). These data confirm that MET is implicated in miR-221 and miR-222 regulation, at least in part through JNK, AP-1 and in particular c-Jun transcription factor.

Example VI

Experimental Procedures

Luciferase Assay

The 3' UTR of the human PTEN and TIMP3 genes were PCR amplified using the following primers: PTEN Fw 5'-TCT AGA GAC TCT GAT CCA GAG AAT GAA CC-3' [SEQ ID No:1] and PTEN Rw 5'-TCT AGA GTT GCC ACA AGT GCA AAG GGG TAG GAT GTG-3' [SEQ ID No:2]; TIMP3 Fw 5'-TCT AGA CTG GGC AAA GAA GGG TCT TTC GCA AAG C-3' [SEQ ID No:3] and TIMP3 Rw 5' TCT AGA TTC CAA TAG GGA GGA GGC TGG AGG AGT CTC-3' [SEQ ID No:4] and cloned downstream of the Renilla luciferase stop codon in pGL3 control vector (Promega), giving rise to the p3'UTR-PTEN and p3'UTR-TIMP3 plasmids.

These constructs were used to generate, by inverse PCR, the p3'-UTRmut-PTEN plasmid-primers: Fw: 5'-GTT GAA AAA AGG TTG GGG GCG GGT GTC ATG TAT ATA C-3 [SEQ ID No:5]; Rw: 5'-GTA TAT ACA TGA CAC CCG CCC CCA ACC TTT TTT CAA C-3'[SEQ ID No:6]; p3'-UTRmut-TIMP3 plasmid-primers: Fw: 5'-GTA TAA TTT AAA ATC ATT GGG CGG CGG GAG ACA CTT CTG TAT TTC-3' [SEQ ID No:7]; Rw: 5'-GAA ATA CAG AAG TGT CTC CCG CCG CCC AAT GAT TTT AAA TTA TAC-3' [SEQ ID No:8].

MeG01 cells were cotransfected with 1 µg of p3'UTR-PTEN or p3'UTR-TIMP3 and with p3'UTRmut-PTEN or p3' UTR TIMP3 plasmids and 1 µg of a Renilla luciferase expression construct pRL-TK (Promega) by using Lipofectamine 2000 (Invitrogen). Cells were harvested 24 h post-transfection and assayed with Dual Luciferase Assay (Promega) according to the manufacturer's instructions. Three independent experiments were performed in triplicate.

Lung and Liver Cancer Samples and Cell Lines.

A total of 32 snap-frozen normal and malignant lung tissues (19 men and 13 women, median age: 70.0, range: 55-82) and 60 snap-frozen normal and 60 malignant liver tissues were collected at the Ohio State University Medical Center (Columbus, Ohio). Other 72 cancer and normal (24) lung tissues were purchased from US Biomax, Inc. All human tissues were obtained according to a protocol approved by the Ohio State Institutional Review Board.

In Vivo Experiments.

Animal studies were performed according to institutional guidelines. NCI-H460 cells were stable transfected by using shPTEN and TIMP3 plasmids (Santa Cruz); Calu-1 cells were stable transfected with shMET. After the selection in puromycin for 10 days 5 106 (H460) or 7106 (Calu-1) viable cells were injected s.c. into the right flanks of 6-wk-old male nude mice (Charles RiverBreeding Laboratories, Wilmington, Mass.). Treatment started five days (H460 xenograft) or ten days (Calu-1 xenograft) from tumor cell inoculation by daily ip injections of TRAIL/Apo2 (10 mg/kg/d) or vehicle (PBS) for two cycles of 5 days. Tumor size was assessed every five days by a digital caliper. The tumor volumes were determined by measuring the length (1) and the width (w) and calculating the volume (V=lw2/2). 35 days after injection, mice were sacrificed and tumors samples were analyzed by western blot for PTEN, TIMP3 and MET expression. Statistical significance between control and treated animals was evaluated by using Student's t test. Animal experiments were conducted after approval of the Institutional animal care and use committee, Ohio State University.

Statistical Analysis

Student's t-test and One-way ANOVA analysis was used to determine significance. All error bars represent the standard error of the mean. Pearson correlation coefficient was calculated to test the association between miR-221/miR-222 and PTEN in the classes Normal versus Tumor. Statistical significance for all the tests, assessed by calculating P-value, was <0.05.

Western Blot Analysis.

Total proteins from NSCLC and HCC cells were extracted with radioimmuno-precipitation assay (RIPA) buffer (0.15 mM NaCl, 0.05 mM Tris-HCl, pH 7.5, 1% Triton, 0.1% SDS, 0.1% sodium deoxycholate and 1% Nonidet P40). Sample extract (50 µg) was resolved on 7.5-12% SDS-polyacrylamide gels (PAGE) using a mini-gel apparatus (Bio-Rad Laboratories) and transferred to Hybond-C extra nitrocellulose. Membranes were blocked for 1 h with 5% nonfat dry milk in Tris-buffered saline containing 0.05% Tween 20, incubated overnight with primary antibody, washed and incubated with secondary antibody, and visualized by chemiluminescence.

The following primary antibodies were used: anti-PTEN, anti-c-Jun, anti-p-c-Jun, anti-Fos, anti-p-JNK, anti-MMP3, anti-Mc1-1 (Santa Cruz), anti-TIMP3 (Millipore) anti-PI3K (BD Biosciences), anti-ERKs, anti-phospho ERKs, anti-AKT, anti-p-AKT, anti-GSK3b, anti-p-GSK3b (Ser9), anti-PAK1 anti-caspase-8,-3 and -9, anti-PARP, anti-cytochrome c (Cell signaling) and anti-MMP9, anti-FADD (Abcam), anti-1-actin antibody (Sigma). A secondary anti-rabbit or anti-mouse immunoglobulin G (IgG) antibody peroxidase conjugate (Chemicon) was used.

Luciferase Assay.

DNA fragments containing the putative regulatory region upstream to miR-222/miR-221 (from +1~−150 nt, +1~−600, +1~−1000 (+1 position corresponds to the 5' terminus of miR-222 hairpin) were amplified and cloned in pGL3basic (Promega). Meg01 cells were transfected with Lipofectamine 2000 (Invitrogen), 1.0 g of pGL3basic empty vector or of pGL3 containing the above genomic fragments, 200 ng of Renilla luciferase expression construct pRL-TK (Promega) and MET, c-Jun, c-Fos siRNAs. After 48 h, 4 cells were lysed and assayed with Dual Luciferase Assay (Promega) according to the manufacturer's instructions. Three independent experiments were performed in triplicate. The primers utilized for the cloning were the followings:

```
-1000 pGL3b Forw:
                                         [SEQ ID No: 9]
5' gctagccctagccaccttatcgaaaatagcattcc 3';

-600 pGL3b Forw:
                                         [SEQ ID No: 10]
5' gctagcctgacatgctagtgagcacctgc 3';
```

-continued

```
-150 pGL3b Forw:
                                           [SEQ ID No: 11]
  5' gctagcccagaggttgtttaaaattacgta 3';

miR-222 pGL3b Rev:
                                           [SEQ ID No: 12]
  5' ctcgagagctgggtgatcctttgccttctg 3'.
```

Real-Time PCR

Real-time PCR was performed using a standard TaqMan PCR Kit protocol on an Applied Biosystems 7900HT Sequence Detection System (Applied Biosystems). The 10 µl PCR reaction included 0.67 µl RT product, 1 µl TaqMan Universal PCR Master Mix (Applied Biosystems), 0.2 mM TaqMan probe, 1.5 mM forward primer and 0.7 mM reverse primer. The reactions were incubated in a 96-well plate at 95° C. for 10 mM, followed by 40 cycles of 95° C. for 15 s and 60° C. for 1 min. All reactions were run in triplicate. The threshold cycle (CT) is defined as the fractional cycle number at which the fluorescence passes the fixed threshold. The comparative CT method for relative quantization of gene expression (Applied Biosystems) was used to determine miRNA expression levels. The y axis represents the 2(-CT), or the relative expression of the different miRs. miRs expression was calculated relative to U44 and U48 rRNA and multiplied by 104. Experiments were carried out in triplicate for each data point, and data analysis was performed by using software (Bio-Rad).

RNA Extraction and Northern Blotting

Total RNA was extracted with TRIzol solution (Invitrogen according to the manufacturer's instructions and the integrity of RNA was assessed with an Agilent BioAnalizer 2100 (Agilent, Palo Alto, Calif., USA). Northern blotting was performed as described by Calin et al., 2002. The oligonucleotides used as probes were the complementary sequences of the mature miRNA (miRNA registry):

```
        miR-221,
                                           [SEQ ID No: 13]
        5'-GAAACCCAGCAGACAATGTAGCT-3', miR-222,
                                           [SEQ ID No: 14]
        5'GAGACCCAGTAGCCAGATGTAGCT-3'.
```

Antisense Inhibition of miRNA Expression.

2'-O-methyl (2'-O-me) oligoribonucleotides were synthesized by Fidelity. The sequences of 2'-O-me-anti-miR-221 and 2'-O-me-anti-miR-222 are as follows:

```
                                           [SEQ ID No: 15]
        5'-gaaacccagcagacaauguagcu
        and
                                           [SEQ ID No: 16]
        5'-gagacccagtagccagatgtagct.
```

2'-O-me-GFP miR (5'-aaggcaagcugacccugaagu [SEQ ID No:17]) was used as control. Cells were grown in six well plate (1.7×10$^6$ per well) for 24 h and transfected 100 nmoli/L/well of 2'-O-me-oligoribonucleotides using lipofectamine 2000. RNA and proteins were extracted after 72 h from the transfection.

Cell Death and Cell Proliferation Quantification

Cells were plated in 96-well plates in triplicate and incubated at 37° C. in a 5% $CO_2$ incubator. Super-Killer TRAIL (Alexis Biochemicals) was used for 24-48 h at 400 ng ml-1. Cell viability was examined with 3-(4,5-dimethylthiazol-2-yl)-2,5-dipheniltetrazolium bromide (MTT)-Cell Titer 96 AQueous One Solution Cell Proliferation Assay (Promega), according to the manufacturer's protocol. Metabolically active cells were detected by adding 20 µl of MTT to each well. After 1 h of incubation, the plates were analyzed in a Multilabel Counter (Bio-Rad Laboratories). Apoptosis was assessed using Annexin V-FITC apoptosis detection kits followed by flowcytometric analysis and caspase 3/7 activity. Cells were seeded at 1.8106 cells per 100 mm dish, grown overnight in 10% FBS/RPMI, washed with phosphate-buffered saline (PBS) and then treated for 24 h with 400 ng/ml TRAIL. Following incubation, cells were washed with cold PBS and removed from the plates by trypsinization. The resuspended cells were washed with cold PBS and stained with FITC-conjugated annexin V antibody according to the manufacturer's instructions (Roche Applied Science). Cells (5×10$^5$ per sample) were then subjected to flow cytometric analysis. Flow cytometry analyses were done as described (Garofalo et al., 2007). The fraction of H460 cells treated with TRAIL was taken as the apoptotic cell population. The percentage of apoptosis indicated was corrected for background levels found in the corresponding untreated controls. Statistical analysis was done using two sample t test, assuming equal variance, and P value was calculated based on two-tailed test. For detection of caspase 3/7 activity, cells were cultured in 96-well plates and treated with TRAIL 400 ng/ml and analyzed using Caspase-Glo 3/7 Assay kit (Promega) according to the manufacturer's instructions. Continuous variables are expressed as mean values±standard deviation (s.d.).

Chromatin Immunoprecipitation.

Chromatin immunoprecipitation was performed as described by de Belle et al., 2000 with slight modifications. Cells (5106) from H460, Calu-1 and Snu-387 cell lines were fixed in 1% formaldehyde for 10 min at 37° C. Cells were washed with ice-cold 1 PBS, scraped in 1×PBS plus protease inhibitors, and collected by centrifugation. Cell pellets, resuspended in cell lysis buffer [50 mmol/L Tris-HCl (pH 8.0), 10 mmol/L EDTA, and 1% SDS] plus protease inhibitors, were then sonicated. DNA-protein complexes were immunoprecipitated using 5 g of the anti-c-Jun antibody (Santa Cruz) or with rabbit polyclonal IgG control (Zymed).

Cross-links in the immunoprecipitated chromatin were reversed by heating with proteinase K at 65° C. overnight, and DNA was purified by the MinElute Reaction Cleanup column (Qiagen) and resuspended in water. The purified chromatin was subjected to PCR and the products were analyzed by gel electrophoresis using 2% agarose. The following primers were used:

```
        Region1F:
                                           [SEQ ID No: 18]
        5' GATGTGGAGAATAGATACCTTTGAG 3'

Region1R:
                                           [SEQ ID No: 19]
        5' GGCACTGCCTACAAACCAGAGCATA 3'

Region2F:
                                           [SEQ ID No: 20]
        5' GTCACTCAGTCAGTATCTGTTGGA 3'

Region2R:
                                           [SEQ ID No: 21]
        5' GTGTGTAATTCAAGGTAAAGTTTTC 3'
```

Anti-PTEN and anti-TIMP3 siRNAs transfection.

Cells were cultured to 80% confluence and transiently transfected using Lipofectamine 2000 with 100 nM anti-PTEN or with 100 nM anti-TIMP3 SMARTpool siRNAs or control siRNAs (Dharmacon), a pool of four target specific 20-25 nt siRNAs designed to knock down gene expression.

miRNA locked nucleic acid in situ hybridization of formalin fixed, paraffin-embedded tissue section.

In situ hybridization (ISH) was carried out on deparaffinized human lung and liver tissues using previously published protocol (Nuovo et al., 2009), which includes a digestion in pepsin (1.3 mg/ml) for 30 minutes. The sequences of the probes containing the six dispersed locked nucleic acid (LNA) modified bases with digoxigenin conjugated to the 5' end were:

```
miR-221,
                                    [SEQ ID No: 13]
5'-GAAACCCAGCAGACAATGTAGCT, miR-222,
                                    [SEQ ID No: 14]
5'GAGACCCAGTAGCCAGATGTAGCT.
```

The probe cocktail and tissue miRNA were co-denatured at 60° C. for 5 minutes, followed by hybridization at 37° C. overnight and a low stringency wash in 0.2×SSC and 2% bovine serum albumin at 4° C. for 10 minutes. The probe-target complex was seen due to the action of alkaline phosphatase on the chromogen nitroblue tetrazolium and bromochloroindolyl phosphate (NBT/BCIP). Negative controls included the use of a probe which should yield a negative result in such tissues. No counterstain was used, to facilitate co-labeling for PTEN, TIMP3 and MET proteins. After in situ hybridization for the miRNAs, as previously described (Nuovo et al., 2009), the slides were analyzed for immunohistochemistry using the optimal conditions for PTEN (1:800, cell conditioning for 30 minutes), TIMP3 (1:1300, cell conditioning for 30 minutes) and MET (1:20, cell conditioning for 30 minutes). For the immunohistochemistry, the inventors used the Ultrasensitive Universal Fast Red system from Ventana Medical Systems. The inventors used normal liver and lung tissues as controls for these proteins. The percentage of tumor cells expressing PTEN, TIMP3 and miR-221 and miR-222 was then analyzed with emphasis on co-localization of the respective targets (miR-221 or miR-222 and either PTEN or TIMP3).

Materials.

Media, sera and antibiotics for cell culture were from Life Technologies, Inc. (Grand Island, N.Y., USA). Protein electrophoresis reagents were from Bio-Rad Laboratories (Richmond, Va., USA) and western blotting and ECL reagents from GE Healthcare (Piscataway, N.J., USA). All other chemicals were from Sigma (St Louis, Mo., USA).

Lung and Liver Cancer Samples and Cell Lines.

Human Calu-1 and A549 cell lines were grown in Dulbecco's modified Eagle's medium containing 10% heat-inactivated fetal bovine serum (FBS) and with 2 mM L-glutamine and 100 Uml-1 penicillin-streptomycin. He1299, H460, A459, H1975, H1299, H1573, H23, PLCRF15, SNU-387, Snu-423, Snu-475 cell lines were grown in RPMI containing 10% heat-inactivated FBS and with 2 mM L-glutamine and 100 Uml-1 penicillin-streptomycin. Sk-hep1, Hep-G2, HepG2C3A, Hep3B, Huh7 were grown in MEM supplemented with 10% fetal bovine serum, 2 mM L-glutamine and 100 Uml-1 penicillin-streptomycin. Normal Hepatocytes were grown in Hepatocytes growth medium (Sciencell) supplemented with 10% fetal bovine serum, 2 mM L-glutamine, 1% of hepatocyte growth supplement (HGS) and 100 Uml-1 penicillin-streptomycin.

Migration Assay

Transwell insert chambers with 8-nm porous membrane (Greiner bio-one) were used for the assay. Cells were washed three times with PBS and added to the top chamber in serum-free media. The bottom chamber was filled with media containing 10% FBS. Cells were incubated for 24 h at 37° C. in a 5% CO2 humidified incubator. To quantify migrating cells, cells on the top chamber were removed by using a cotton-tipped swab, and the migrated cells were fixed in PBS, 25% glutaraldehyde and stained with Crystal Violet stain, visualized under a phase-contrast microscope, and photographed. Cristal violet-stained cells were moreover solubilized in acetic acid and methanol (1:1) and absorbance was measured at 595 nm. The results are means of three independent experiments±S.D.

Invasion Assay

H460 and SK-Hep-1 cells were placed into the top chamber of a BD Falcon HTS FluoroBlok insert with a membrane containing 8-nm pores (BD Biosciences) in 300 L of serum-free Dulbecco's modified Eagle medium in triplicate. The inserts were placed into the bottom chamber wells of a 24-well plate containing Dulbecco's modified Eagle medium media and fetal bovine serum (10%) as chemoattractant. Cells that migrated through the pores of the membrane to the bottom chamber were labeled with 8 g/mL calcein-AM (Molecular Probes, Eugene, Oreg.) in phosphate-buffered saline (PBS) for 30 minutes at 37° C. The fluorescence of migrated cells was quantified using a fluorometer at excitation wavelengths of 485 nm and emission wavelengths of 530 nm and expressed as arbitrary fluorescence units. Data are expressed as mean±standard error of 4 separate determinations.

PTEN and TIMP3 Plasmids.

PTEN and TIMP3 cDNAs were obtained from H460 cells RNA by using the one step RT-PCR kit (Invitrogen) according to the manufacturer's instructions. The PCR fragments were amplified by using the following primers:

```
NotI-TIMP3-HA:
                                    [SEQ ID No: 22]
5' gcggccgcatgacccttggctcgggctcatcgtgct 3'

BglII-TIMP3-HA:
                                    [SEQ ID No: 23]
5' agatctcagggtctggcgctcaggggtctgt 3'

NotI-PTEN-HA:
                                    [SEQ ID No: 24]
5' gcggccgcatgacagccatcatcaaagagatcgttag 3'

XbaI-PTEN-HA:
                                    [SEQ ID No: 25]
5' tctagaggtgttttatccctcttgataaaaaaaattca 3'
``` and then cloned in pCRUZ-HA (Santa Cruz) after digestion with NotI-XbaI (PTEN) or NotI-BglII (TIMP3). All vectors were controlled by sequencing.

Target Analysis

Bioinformatic analysis was performed by using these specific programs: Targetscan1, Pictar2 and RNhybrid3. 1 http://www.targetscan.org/2 http://pictar.bio.nyu.edu/3 http://bibiserv.techfak.uni-bielefeld.de/

Example VII

Method of Treating HCC in Patients Exhibiting TRAIL Sensitive TRAIL Expression Pattern in HCC Tumor Samples This example describes a method of selecting and treating HCC patients that are likely to have a favorable response to TRAIL treatment as a therapy.

For some HCC patients, TRAIL therapy can prolong survival (Sun et al., J. Cancer Res. Clin. Oncol. 132(7):458-465, 2006). However, it would be beneficial to identify patients that are most likely to benefit from TRAIL therapy prior to initiating treatment.

It is now disclosed herein that the prognosis of HCC patients expressing TRAIL sensitive TRAIL Expression Pattern in tumor samples relative to a control (such as non-cancerous liver tissue obtained from the same patient) significantly improves after treatment with TRAIL. In contrast, patients expressing TRAIL resistant TRAIL Expression Pattern in tumor samples do not exhibit a significant increase in survival following TRAIL treatment and thus are not good candidates for such adjunctive treatment.

A patient diagnosed with HCC first undergoes liver resection with an intent to cure. HCC tumor and non-cancerous tissue samples are obtained from the portion of the liver tissue removed from the patient. RNA is then isolated from the tissue samples using any appropriate method for extraction of small RNAs that are well known in the art, such as by using TRIZOL™. Purified RNA is then subjected to RT-PCR using primers specific for c-Jun and miR-221 and miR-222, optionally in conjunction with PTEN and/or TIMP3. The assay may also be run with miR-221 and miR-222 and PTEN and/or TIMP3, without c-Jun. These assays are run to determine the expression level of the pertinent RNA in the tumor and non-cancerous tissues. If TRAIL sensitive Expression Pattern is found in the tumor tissue relative to the non-cancerous tissue, the patient is a candidate for TRAIL adjunctive therapy.

Accordingly, the patient is treated with a therapeutically effective amount of TRAIL a according to methods known in the art. The dose and dosing regimen of TRAIL will vary depending on a variety of factors, such as health status of the patient and the stage of the HCC. Typically, TRAIL is administered in many doses over time.

Example VIII

Alternative Treatment Method for HCC Patients with Low Expression of miR-26

This example describes a method of treating a patient diagnosed with HCC in the absence of liver resection. To determine whether a patient diagnosed with HCC is a good candidate for TRAIL therapy, a HCC tumor sample is obtained from the patient that has not undergone liver resection, along with a non-cancerous liver tissue sample. The tissue samples can be obtained according to any method known in the art. For example, the tissue samples can be obtained by performing a biopsy procedure using a hypodermic needle to remove the desired tissues.

RNA is then isolated from the tissue samples using any appropriate method for extraction of small RNAs that are well known in the art, such as by using TRIZOL™. Purified RNA is then subjected to RT-PCR using primers specific for miR-26 to determine the expression level of miR-26 in the tumor and non-cancerous tissues. If TRAIL sensitive TRAIL Expression Pattern is found in the tumor tissue relative to the non-cancerous tissue, the patient is a candidate for therapy.

Accordingly, the patient is treated with a therapeutically effective amount of therapeutic according to methods known in the art. The dose and dosing regimen will vary depending on a variety of factors, such as health status of the patient and the stage of the HCC. Typically, treatment is administered in many doses over time.

Example IV

Method of Treating HCC in Patients Exhibiting TRAIL Resistant TRAIL Expression Pattern in HCC Tumor Samples This example describes a method of treating a patient diagnosed with HCC if the patient exhibits a TRAIL resistant TRAIL Expression Pattern in the HCC tumor.

A patient diagnosed with HCC first undergoes liver resection with an intent to cure. HCC tumor and non-cancerous tissue samples are obtained from the portion of the liver tissue removed from the patient. RNA is then isolated from the tissue samples using any appropriate method for extraction of small RNAs that are well known in the art, such as by using TRIZOL™. Purified RNA is then subjected to RT-PCR using primers specific for miR-26 to determine the expression level of miR-26 in the tumor and non-cancerous tissues. If TRAIL resistant TRAIL Expression Pattern is found in the tumor tissue relative to the non-cancerous tissue, the patient is unlikely to respond favorably to TRAIL adjunctive therapy. Accordingly, the patient does not receive TRAIL therapy but is considered for other treatment modalities to convert to TRAIL sensitivity. Alternatively, the patient is monitored for post-operative signs of disease recurrence.

Example IX

Methods of Diagnosing HCC Patients

In one particular aspect, there is provided herein a method of diagnosing whether a subject has, or is at risk for developing, hepatocellular carcinoma (HCC). The method generally includes measuring the TRAIL Expression Pattern in a test sample from the subject and determining whether the TRAIL Expression Pattern in the test sample deviates relative to the level of a TRAIL Expression Pattern in a control sample, is indicative of the subject either having, or being at risk for developing, HCC. In certain embodiments, the level of the at least one gene product is measured using Northern blot analysis. Also, in certain embodiments, the level of the at least one gene product in the test sample is less than the level of the corresponding miR gene product in the control sample, and/or the level of the at least one miR gene product in the test sample is greater than the level of the corresponding miR gene product in the control sample.

Example X

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, HCC.

Example XI

Diagnostic and Therapeutic Applications

In another aspect, there is provided herein are methods of treating HCC in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a HCC associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Also provided herein are methods of treating HCC in a subject who has HCC in which at least two gene products of the TRAIL Expression Pattern genes are down-regulated or up-regulated in the cancer cells of the subject relative to control cells. When the at least two gene products are down-regulated in the cancer cells, the method comprises administering to the subject an effective amount of at least two isolated gene products, such that proliferation of cancer cells in the subject is inhibited. When two or more gene products are up-regulated in the cancer cells, the method comprises administering to the subject an effective amount of at least one compound for inhibiting expression of at least one gene product, such that proliferation of cancer cells in the subject is inhibited. Also provided herein are methods of treating HCC in a subject, comprising: determining the amount of at least two TRAIL Expression gene products in HCC cells, relative to control cells; and, altering the amount of the gene products expressed in the HCC cells by: administering to the subject an effective amount of at the at least two gene products, if the amount of the gene products expressed in the cancer cells is less than the amount of the gene products expressed in control cells; or administering to the subject an effective amount of at least one compound for inhibiting expression of the at least two gene products, if the amount of the gene product expressed in the cancer cells is greater than the amount of the gene product expressed in control cells, such that proliferation of cancer cells in the subject is inhibited.

Example XII

Compositions

Also provided herein are pharmaceutical compositions for treating TRAIL resistant cancer, comprising at least two isolated TRAIL Expression Pattern gene product and a pharmaceutically-acceptable carrier. In a particular embodiment, the pharmaceutical compositions comprise gene products corresponds to gene products that are down-regulated in HCC cells relative to suitable control cells.

In another particular embodiment, the pharmaceutical composition comprises at least one expression regulator (for example, an inhibitor) compound and a pharmaceutically-acceptable carrier.

Also provided herein are pharmaceutical compositions that include at least one expression regulator compound that is specific for a gene product that is up- or down-regulated in HCC cells relative to suitable control cells.

Example XIII

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example XIV

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

In view of the many possible embodiments to which the principles of our invention may be applied, it should be recognized that the illustrated embodiments are only preferred examples of the invention and should not be taken as a limitation on the scope of the invention. Rather, the scope of the invention is defined by the following claims. We therefore claim as our invention all that comes within the scope and spirit of these claims.

What is claimed is:

1. A method to alter regulation of TIMP3 expression in a cell capable of expressing TIMP3 and miR-221 and miR-222, comprising contacting the cell with inhibitors of miR-221 and miR-222 in an amount sufficient to increase expression of TIMP in the cell,
wherein the cell is selected from the group consisting of a non-small cell lung carcinoma cell, a hepatocellular carcinoma cell, and a melanoma cell.

2. The method of claim 1, wherein the inhibitor of miR-221 comprises an antisense microRNA to miR-221.

3. The method of claim 2, wherein miR-221 is complementary to SEQ ID NO: 13.

4. The method of claim 1, wherein the inhibitor of miR-221 is complementary to hsa-miR-221 having SEQ ID NO: 28.

5. The method of claim 1, wherein the inhibitor of miR-221 comprises 2'-O-me-anti-miR-221 having SEQ ID NO: 15.

6. The method of claim 1, wherein the inhibitor of miR-222 comprises an antisense microRNA to miR-222.

7. The method of claim 6, wherein miR-222 is complementary to SEQ ID NO: 14.

8. The method of claim 1, wherein the inhibitor of miR-222 is complementary to hsa-miR-222 having SEQ ID NO: 26.

9. The method of claim 1, wherein the inhibitor of miR-222 comprises 2'-O-me-anti-miR-222 having SEQ ID NO: 16.

10. The method of claim 1, wherein the cell is transfected with 2'-O-me-anti-miR-221 having SEQ ID NO: 15 and with 2'-O-me-anti-miR-222 having SEQ ID NO: 16.

11. The method of claim 1, wherein the cell is a mammalian cell.

12. The method of claim 1, wherein the cell is a human cell.

13. The method of claim 1, wherein the inhibitor of miR-222 comprises a nucleotide sequence that is identical to a nucleotide sequence in PTEN-3'UTR having SEQ ID NO: 27.

14. The method of claim 1, wherein the inhibitor of miR-221 comprises a nucleotide sequence that is identical to a nucleotide sequence in TIMP3-3'UTR having SEQ ID NO: 30.

15. The method of claim 1, wherein the method is performed in vivo.

16. The method of claim 1, wherein the inhibitors of miR-221 or miR-222 comprise a contiguous nucleotide sequence which is either identical to, or is fully complementary to, the sequence of the seed region of miR-221 or miR-222.

17. The method of claim 16, wherein the seed region consists of nucleotides 16-22 in SEQ ID NO: 26.

18. The method of claim 16, wherein the seed region consists of nucleotides 15-22 in SEQ ID NO: 26.

19. The method of claim 16, wherein the contiguous nucleotide sequence is fully complementary to the sequence of a promoter region of miR-221, or wherein the contiguous nucleotide sequence is fully complementary to the sequence of a promoter region of miR-221.

20. The method according to claim 16, wherein the contiguous nucleotide sequence comprises between 7 and 22 nucleotides, which are fully complementary to the sequence of the corresponding region of miR-221.

21. The method according to claim 15, wherein the contiguous nucleotide sequence comprises between 7 and 22 nucleotides which are fully complementary to a sequence found in SEQ ID NO: 13.

22. The method of claim 16, wherein the contiguous nucleotide sequence is fully complementary to the sequence of a region of miR-222.

23. The method according to claim 16, wherein the contiguous nucleotide sequence comprises between 7 and 22 nucleotides, which are fully complementary to the sequence of the corresponding region of miR-222.

24. The method according to claim 16, wherein the contiguous nucleotide sequence comprises between 7 and 22 nucleotides which are fully complementary to a sequence found in SEQ ID NO: 14.

* * * * *